United States Patent [19]

Nakatsukasa et al.

[11] 4,416,994
[45] Nov. 22, 1983

[54] PLASMID PEL7 AND RELATED CLONING VECTORS FOR USE IN STREPTOMYCES AND RELATED ORGANISMS

[75] Inventors: Walter M. Nakatsukasa; Jeffrey T. Fayerman; James A. Mabe, all of Indianapolis, Ind.

[73] Assignee: Eli Lilly and Company, Indianapolis, Ind.

[21] Appl. No.: 312,446

[22] Filed: Oct. 19, 1981

[51] Int. Cl.³ .................... C12N 1/20; C12N 15/00; C12N 1/00; C12P 21/00; C12P 21/02; C12R 1/465

[52] U.S. Cl. .................... 435/253; 435/172; 435/317; 435/68; 435/70; 435/886

[58] Field of Search .................... 435/172, 68, 70, 253, 435/317, 886

[56] References Cited

U.S. PATENT DOCUMENTS

| | | | |
|---|---|---|---|
| 4,273,875 | 6/1981 | Manis | 435/253 |
| 4,332,898 | 6/1982 | Reusser | 435/317 |
| 4,332,900 | 6/1982 | Manis et al. | 435/317 |
| 4,338,400 | 7/1982 | Manis et al. | 435/317 |
| 4,340,674 | 7/1982 | Manis et al. | 435/317 |
| 4,343,906 | 8/1982 | Reusser et al. | 435/317 |

FOREIGN PATENT DOCUMENTS 7901169 12/1979 United Kingdom .
2048894 12/1980 United Kingdom .

OTHER PUBLICATIONS

Bolivar et al., Gene 2, 95 (1977).
American Type Culture Collection Catalogue–1982.
Hopwood et al. in *Plasmids of Medical, Environmental and Commercial Importance*, Timmis et al., (Ed.), Elsevier North Holland, 1979, pp. 245–258.
Bibb, M. et al., 1980, Nature 284:526.
Thompson, C. et al., 1980, Nature 286:525.
Thompson, C. and Cundliffe, E., 1980, J. of Bacteriology, 142(2):455.
Bibb, M. et al., 1980, Developments in Industrial Microbiology 21:55.
Gray, O. et al., 1980, Abstracts of the 80th Annual ASM Meeting, Paper No. H68.

*Primary Examiner*—Thomas G. Wiseman
*Assistant Examiner*—James Martinell
*Attorney, Agent, or Firm*—Gerald V. Dahling; Arthur R. Whale

[57] ABSTRACT

The present invention discloses selectable pairs of recombinant DNA cloning vectors for use in Streptomyces and related organisms.

70 Claims, 14 Drawing Figures

Restriction Site and Functional Map of Plasmid pEL7

Restriction Site and Functional Map of Plasmid pEL7

Restriction Site and Functional Map
of Plasmid pLR1

Restriction Site and Functional Map
of Plasmid pLR2**

Restriction Site and Functional Map of Plasmid pLR4

Restriction Site and Functional Map of Plasmid pEL7.1

Restriction Site and Functional Map of Plasmid pEL7.2

Restriction Site and Functional Map of Plasmid pEL7.3

Restriction Site and Functional Map
of Plasmid pEL7.4**

Restriction Site and Functional Map of Plasmid pEL7.5

Restriction Site and Functional Map
of Plasmid pEL7.6**

Restriction Site and Functional Map of Plasmid pEL7.7

Restriction Site and Functional Map of Plasmid pEL7.8

Restriction Site and Functional Map of Plasmid pLR5

Restriction Site and Functional Map
of Plasmid pLR6**

4,416,994

PLASMID pEL7 AND RELATED CLONING VECTORS FOR USE IN STREPTOMYCES AND RELATED ORGANISMS

The present invention comprises novel pairs of recombinant DNA cloning vectors, each pair comprising plasmid pEL7 and a second plasmid comprising a restriction fragment of plasmid pEL7 and one or more DNA segments that convey resistance to antibiotics. The invention further comprises transformants of the aforementioned pairs of vectors.

The present invention provides antibiotic resistance conferring cloning vectors for use in Streptomyces and related host cells. Heretofore, the development and exploitation or recombinant DNA technology in the above organisms has been retarded and made especially difficult because of the general lack of selectable genetic markers on cloning vectors. The vectors of the present invention are functional and selectable in both Streptomyces and other host strains and therefore represent a significant advance in the technical art.

The present vectors are particularly useful because they are versatile and can be transformed and selected in any Streptomyces cell that is sensitive to an antibiotic for which resistance is conveyed. Since a high proportion of the clinically important antibiotics are produced by Streptomyces strains, it is especially desirable to develop cloning systems and vectors that are applicable to that industrially important group. The present invention provides such vectors and thus allows for the cloning of genes into Streptomyces for increasing the yields of known antibiotics as well as for the production of new antibiotics and antibiotic derivatives.

The present invention provides vehicles for cloning DNA into Streptomyces host cells and also allows for the convenient selection of transformants. Since transformation is a very low frequency event, such a functional test is a practical necessity for determining which cell(s), of among the millions of cells, has acquired in the plasmid DNA. This is important because DNA sequences that are non-selectable can be inserted onto the vectors and, upon transformation, cells containing the vector and the particular DNA sequence of interest can be isolated by appropriate antibiotic selection.

For purposes of the present invention as disclosed and claimed herein, the following terms are as defined below.

Recombinant DNA Cloning Vector - any autonomously replicating agent, including but no limited to plasmids, comprising a DNA molecule to which one or more additional DNA segments can or have been added.

Transformation - the introduction of DNA into a recipient host cell that changes the genotype and consequently results in a stable and heritable change in the recipient cell.

Transformant - a recipient host cell that has undergone transformation.

Sensitive Host Cell - a host cell that cannot grow in the presence of a given antibiotic without a DNA segment that confers resistance thereto.

Restriction Fragment - any linear portion or whole of a plasmid generated by the action of one or more restriction enzymes on the plasmid.

Functionally Dependent - the condition whereupon plasmid replication and expression of resistance to one or more antibiotics requires the presence of a separate and different plasmid.

Insertional Isomer - one of two or more possible recombinant DNA molecules formed when a DNA fragment is inserted at one of two or more compatible sites on the recipient DNA.

Plasmid pLR2 1.6 kB BamHI Restriction Fragment - the same 1.6 kb BamHI thiostrepton resistance conferring fragment contained in plasmid pIJ6.

Plasmid pLR1 or pLR4 3.4 kb BamHI Restriction Fragment - the same 3.4 kb BamHI neomycin resistance conferring fragment contained in plasmid pIJ2.

Plasmid pLR1 3.5 kb PstI Restriction Fragment - the same 3.5 kb PstI neomycin resistance conferring fragment contained in plasmid pIJ2.

$Amp^R$ - the ampicillin resistant phenotype.
$Tet^S$ - the tetracycline sensitive phenotype.
$Thio^R$ - the thiostrepton resistant phenotype.
$Neo^R$ - the neomycin resistant phenotype.

DETAILED DESCRIPTION OF THE INVENTION

The present invention comprises novel pairs of recombinant DNA cloning vectors, each pair comprising:
(a) novel plasmid pEL7, and
(b) a second plasmid that is functionally dependent upon plasmid pEL7, said second plasmid comprising a restriction fragment of plasmid pEL7 and one or more different DNA segments that convey resistance to at least one antibiotic when transformed into a sensitive host cell, said host cell being susceptible to transformation, cell division, and culture.

The invention further comprises transformants of the aforementioned pairs of vectors.

Vectors of the present invention are constructed by ligating one or more antibiotic resistance conferring DNA segments onto a restriction fragment of plasmid pEL7. Plasmid pEL7, from which the restriction fragments are constructed, is approximately 10.9 kb and contains several restriction sites which are particularly advantageous for molecular cloning. Since the resistance conferring vectors of the present invention are functionally dependent on plasmid pEL7, a variety of different pEL7 restriction fragments can be used for their construction without regard for independent functionality. Thus, plasmid pEL7, useful directly as a cloning vector, is essential for both the construction and functioning of the present invention. A detailed restriction site and functional map of plasmid pEL7 is presented in FIG. 1 of the accompanying drawings. For purposes of the present application, FIG. 1 and all subsequent figures are not drawn to scale.

Plasmid pEL7 can be conventionally isolated from Streptomyces ambofaciens/pEL7, a constructed strain deposited and made part of the stock culture collection of the Northern Regional Research Laboratory, Peoria, Ill. It is available to the public, as a source and stock reservoir of the plasmid under the accession number NRRL 12523.

Although many different restriction fragments of plasmid pEL7 can be constructed, those exemplified herein for illustrative purposes, include the 10.9 kb BamHI and the 10.9 kb PstI restriction fragments. These fragments are ligated to one or more antibiotic resistance conferring DNA fragments, exemplified herein for illustrative purposes by the thiostrepton resistance conferring 1.6 kb BamHI restriction fragment of plasmid pLR2 and the neomycin resistance conferring 3.5 kb PstI restriction fragment of plasmid pLR1, to form vectors illustrative of the present invention.

Plasmid pLR2, the source of the thiostrepton resistance conferring fragment, is approximately 18.7 kb and is constructed by ligating HindIII treated plasmid pIJ6, disclosed in Thompson et al., 1980, Nature 286:525, to HindIII treated plasmid pBR322. Plasmid pLR1, the source of the neomycin resistance conferring fragment, is approximately 14.8 kb and is similarly constructed, except that plasmid pIJ2, disclosed in Thompson et al., 1980, is used instead of plasmid pIJ6. Both plasmids pLR2 and pLR1 are functional in *E. coli* and therefore can be amplified and isolated conveniently for subsequent manipulation. An analogous construction, resulting in plasmid pLR4, is made by ligating BamHI treated plasmid pBR322 to BamHI treated plasmid pLR1. A restriction site and functional map of each of plasmids pLR1, pLR2, and pLR4 is presented respectively in FIGS. 2–4 of the accompanying drawings.

For convenience and ease of construction, the thiostrepton resistance conferring 1.6 kb BamHI fragment and the neomycin resistance conferring 3.5 kb PstI fragment are inserted into plasmid pEL7 respectively at the adjacent BamHI and PstI restriction sites. The resulting recombinant DNA is then self ligated to produce plasmids illustrative of the present invention. Recombinant plasmids of two orientations result depending upon the orientation of the inserted DNA fragment. Thus, the insertion of the 1.6 kb BamHI fragment into plasmid pEL7 results in illustrative plasmids pEL7.1 and pEL7.2; insertion of the 3.5 kb PstI fragment results in illustrative plasmids pEL7.3 and pEL7.4; and insertion of both of the fragments results in illustrative plasmids pEL7.5, pEL7.6, pEL7.7, and pEL7.8.

Various plasmid pEL7 restriction sites can be used for the insertion of DNA segments. Therefore, a particular antibiotic resistance conferring DNA segment is not limited to a single position but can be inserted at varying sites provided that the resultant plasmid is functionally dependent on plasmid pEL7.

Although the thiostrepton and neomycin antibiotic resistance conferring DNA segments exemplified herein are respectively the 1.6 kb BamHI and 3.5 kb PstI restriction fragments of plasmids pLR2 and pLR1, those skilled in the art can construct and use, either individually or in combination, additional DNA segments that also confer resistance to thiostrepton and neomycin. Additional thiostrepton resistance conferring DNA segments of plasmid pLR2 include, for example, the 13 kb PstI restriction fragment and also the BclI subfragment of the 1.6 kb BamHI restriction fragment. Additional neomycin resistance conferring DNA segments of plasmid pLR1 include, for example, the 3.4 kb BamHI restriction fragment and also the larger of the SacI-KpnI subfragments of the 3.4 kb BamHI restriction fragment. Still other DNA segments conferring resistance to the same or to different antibiotics such as, for example, chloramphenicol, hygromycin, viamycin, tylosin, erythromycin, and the like can also be constructed and used. In addition, various functional derivatives of the above described antibiotic resistance conferring DNA segments can be constructed by adding, eliminating, or substituting certain nucleotides. Ligation of these derivatives or other antibiotic resistance conferring DNA segments to plasmid pEL7, in place of the resistance conferring DNA segments exemplified herein, results in plasmids that are within the scope of the present invention.

Both the restriction fragments of plasmid pEL7 and the various antibiotic resistance conferring DNA segments can be modified to facilitate ligation. For example, molecular linkers can be provided to either or both of a particular plasmid pEL7 restriction fragment and to particular resistance conferring DNA segments. Thus, specific sites for subsequent ligation can be constructed conveniently. In addition, plasmid pEL7 and the restriction fragments thereof can also be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose.

The present vectors such as, for example, plasmid pEL7 and illustrative plasmids pEL7.1, pEL7.2, pEL7.3, pEL7.4, pEL7.5, pEL7.6, pEL7.7, and pEL7.8 can be ligated to a functional replicon containing and antibiotic resistance conferring restriction fragment of an *E. coli* plasmid such as, for example, plasmid pBR322, pBR324, pBR324, pBR325, and the like, to produce bifunctional plasmids for use in *E. coli* and plasmid pEL7 containing Streptomyces cells. These constructions, exemplified herein by plasmids pLR5 and pLR6, are particularly advantageous because amplification and manipulation of plasmids can be done faster and more conveniently in *E. coli* than in Streptomyces. Thus, after desired recombinant DNA procedures are accomplished within the *E. coli* host system, the particular Streptomyces DNA can be removed, re-constructed to plasmid form, and then transformed into a suitable Streptomyces or related host cell.

The recombinant DNA cloning vectors of the present invention are not limited for use in a single species or strain of Streptomyces. To the contrary, the vectors are broadly applicable and can be transformed into host cells of many Streptomyces taxa, particularly restrictionless strains of economically important taxa that produce antibiotics such as aminoglycoside, macrolide, β-lactam, polyether, and glycopeptide antibiotics. Such restrictionless strains are readily selected and isolated from Streptomyces taxa by conventional procedures well known in the art (Lomovaskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Streptomyces taxa that produce aminoglycoside antibiotics and in which the present vectors are especially useful and can be transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus,* (antibiotic SF733), *S. flavopersicus,* (spectinomycin), *S. spectabilis* (actinospectacin), *S. rimosus* forma paromomycinus (paromomycins, catenulin), *S. fradiae* var. italicus (aminosidine), *S. bluensis* var. *bluensis (bluensomycin), S. catenulae* (catenulin), *S. olivoreticuli* var. *cellulophilus* (destomycin A), I S. tenebrarius (tobramycin, apramycin), *S. lavendulae* (neomycin), *S. albogriseollus* (neomycins), *S. albus* var. metamycinus (metamycin), *S. hygroscopicus* var. sagami-

*ensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. limoneus (validamycins), *S. rimofaciens* (destomycins), *S. hygroscopicus* forma *globosus* (glebomycin), *S. fradiae* (hybrimycins neomycins), *S. eurocidicus* (antibiotic A16316-C), *s. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionsless strains of Strepomyces taxa that produce macrolide antibiotics and in which the present vectors are especially useful and can be transformed, include restrictionless cells of, for example: *S. caelestis* (antibiotic M188), *S. platensis* (platenomycin), *S. rochei* var. volubilis (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (abocycline), *S. roseochromogenes* (albocycline), *S. cinerochromogenes* (cineromycin B), *S. albus* (albomycetin), *S. felleus* (argomycin, picromyclin), *S. rochei* (alnkacidin, borrelidin), *S. violaceoniger* (lankacidin), *S. griseus* (borrelidin), *S. maizeus* (ingramycin), *S. albus* var. *coilmyceticus* (coleimycin), *S. mycarolfaciens* (acetylleukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (formacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibiotics* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. binkiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macroporeus* (carbomycin), *S. thermotolerans* (carbomycin), and *S. albireticuli* (carbomycin).

Preferred host cells of restrictionless strains of Streptomyces taxa that produce β-lactam antibiotics and in which the present vectors are especially useful and can be transformed, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin, A, B), *S. hygroscopicus* (deactoxycephalosporin C), *S. wadayamesnis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, s. flavus, S. fulvoviridis, S. argenteolus,* and *S. sioyaensis* (MM 4550 and MM 13902).

Preferred host cells of restrictionless strains of Streptomyces taxa that produce polyether antibiotics and in which the present vectors are especially useful and can be transformed, include restrictionless cells of, for example: *S. albus* (A204, A28695A and B, salinomycin), *S. hygroscopicus* (A218, emericid, DE3936), A120A, A286-95A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present vestors are especially useful and can be transformed, include restrictionless cells of, for example: *S. orientalis* and *S. haranomachiensis* (vancomycin); *S. candidus* (A-35512, (avoparcin), and *S. eburosporeus* (LL-AM 374).

Preferred host cells of other Streptomyces restrictionless strains in which the present vectors are especially useful and can be transformed include restrictionless cells of, for example: *S. coelicolor, S. granuloruber, S. roseosporus, S. lividans, S. espinosus,* and *S. azureus.*

In addition to the representative Streptomyces host cells described above, the present vectors are also useful and can be transformed into cells of restrictionless stains of other taxa such as, for example: Bacillus, Staphylococcus, and related Actinomycetes, including Streptosporangium, Actinoplanes, Nocardia, and Micromonospora. Thus, the vectors of the present invention have wide application and are useful and can be transformed into host cells of a variety of organisms.

While all the embodiments of the present invention are useful, some of the present recombinant DNA cloning vectors and transformants are more preferred than others. Accordingly, preferred vectors are plasmids pEL7, pEL7.1, pEL7.3, pEL7.5, pLR1, and pLR2; preferred pairs of vectors are plasmids pEL7 and pEL7.1, pEL7 and pEL7.3, and pEL7 and pEL7.5; and preferred transformants are *Streptomyces ambofaciens/*pEL7, *S. ambofaciens/*pEL7, pEL7.1, *S. ambofacins* pEL7, pEL7.3, *S. ambofaciens/*pEL7, pEL7.5, *E. coli* K12 HB101/pLR1, and *E. coli* K12 HB101/pLR2. Moreover, of this preferred group, plasmid pEL7, plasmid pairs pEL7 and pEL7.1, and pEL7 and pEL7.5, and transformants *S. ambofaciens/*pEL7, *S. ambofaciens/*pEL7, pEL7.1, and *S. ambofaciens/*pEL7, pEL7.5 are most preferred.

The recombinant DNA cloning vectors and transformers of the present invention have broad utility and help fill the need for suitable cloning vehicles for use in Streptomyces and related organisms. Moreover, the ability of the present vectors to confer resistance to antibiotics that are toxic to non-transformed host cells, also provides a functional means for selecting transformers. This is important because of the practical necessity for determining and selecting the particular cells that have acquired vector DNA. Additional DNA segments, that lack functional tests for their presence, can also be inserted onto the present vectors and then transoformants containing the non-selectable DNA can be isolated by appropriate antibiotic selection. Such non-selectable DNA segments include, but are not limited to, genes that specify antibiotic modification enzymes and regulatory genes of all types.

More particularly, a non-selectable DNA segment that comprises a gene is inserted on a plasmid such as for example, illustrative plasmid pEL7.5, at the PvuII restriction site of the 1.6 kb BamHI resistance conferring fragment. Such an insertion inactivates the thiostrepton resistance gene and thus allows for the easy identification of transformants containing the recombinant plasmid. This is done by first selecting for neomycin resistance and, secondarily, identifying those neomycin resistant transformants that are not resistant to thiostrepton. In a similar manner, insertion of a DNA segment of interest at, for example, the KpnI restriction site of the 3.5 kb PstI resistance conferring fragment inactivates the neomycin resistance gene. Thus, transformants carrying this recombinant plasmid also are identified easily by first selecting for thiostrepton resistance and, secondarily, identifying those thiostrepton resistant transformants that are not resistant to neomycin. Therefore, the ability to select for antibiotic resistance in Streptomyces and related cells allows for the efficient isolation of the extremely rare cells that contain the particular non-selectable DNA of interest.

The functional test for antibiotic resistance, as described herein above, is also used to search vast quantities of DNA for those segments that can act as control elements and direct expression of an individual antibiotic resistance gene. Such segments, including but not limited to, promoters, attenuators, repressors, inducers, ribosomal binding sites, and the like, are used to control the expression of other genes in cells of Streptomyces and related organisms.

The thiostrepton and neomycin resistance conferring vectors of the present invention are also useful for insuring that linked DNA segments are stably maintained in host cells over many generations. These genes or DNA fragments, covalently linked to the thiostrepton or neomycin resistance conferring fragment and propagated either in Streptomyces or in the cells of related organisms, are maintained by exposing the transformants to levels of thiostrepton or neomycin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Apramycin, Tobramycin, Erythromycin, and the like. The present invention also provides selectable vectors that are useful for cloning, characterizing, and reconstructing DNA sequences that code for commercially important proteins such as, for example, human insulin, human proinsulin, glucagon, interferon, and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, Streptomycin, Cephalosporin, Tylosin, Actaplanin, Narasin, Monensin, Apramycin, and Erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

Streptomyces ambofaciens/pEL7, as a source of plasmid pEL7, can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonia, calcium, phosphate, chloride, sulfate, and like ions. As is necessary for the growth and development of other microorganisms, essential trace elements are also added. Such trace elements are commonly supplied as impurities incidental to the addition of other constituents of the medium.

Streptomyces ambofaciens/pEL7 is grown under aerobic culture conditions over a relatively wide pH range of about 5 to 9 at temperatures ranging from about 15° to 40° C. For production of plasmid pEL7 at the highest copy number, however, it is desirable to start with a culture medium at a pH of about 6.5 and maintain a culture temperature of about 30° C. Culturing Streptomyces ambofaciens/pEL7, under the aforementioned conditions, results in a reservoir of cells from which plasmid pEL7 is isolated conveniently.

Figure 1:
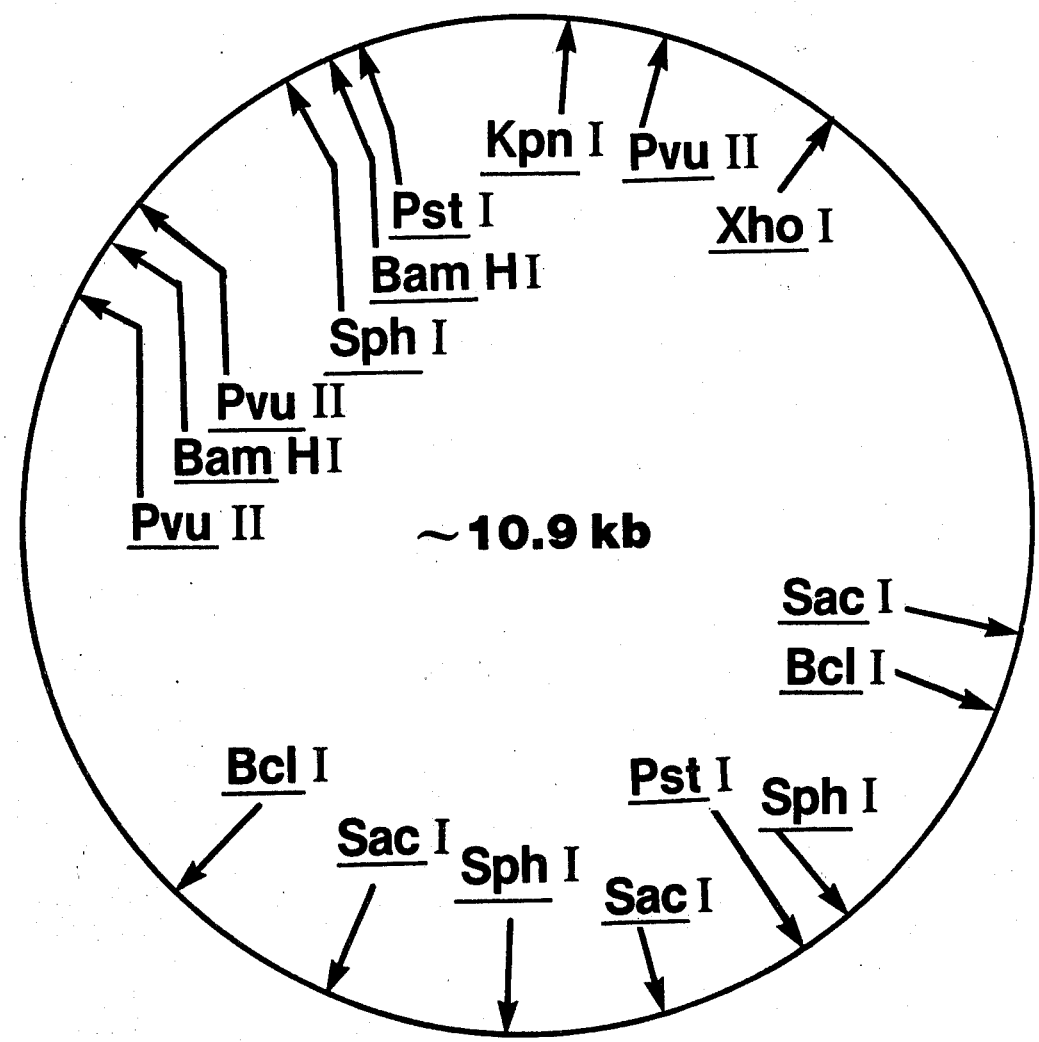
FIG. 1 shows the resitriction site map of plasmid pEL7.
Figure 2:
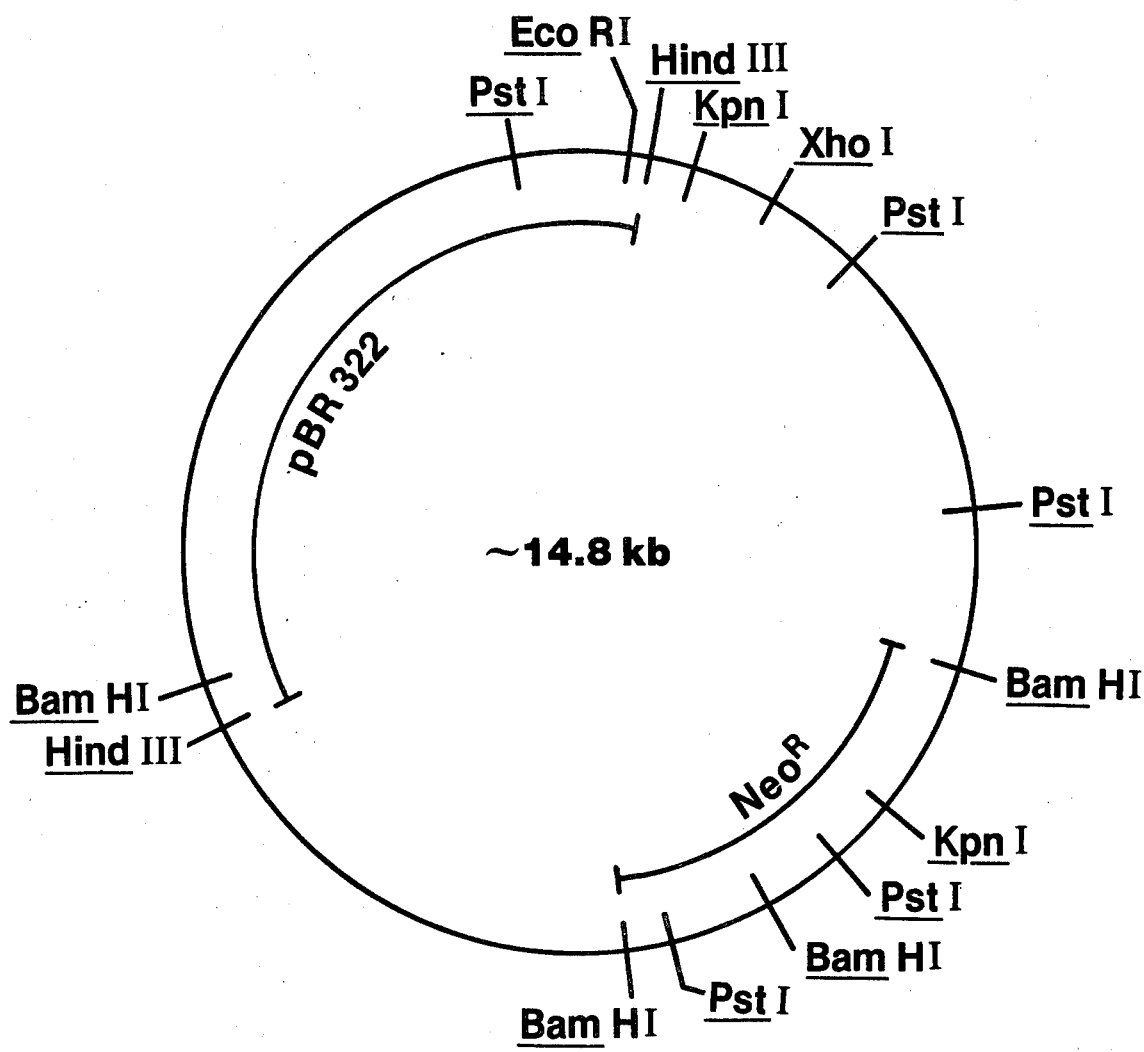
FIG. 2 is a restriction site map of plasmid pLR1.
Figure 3:
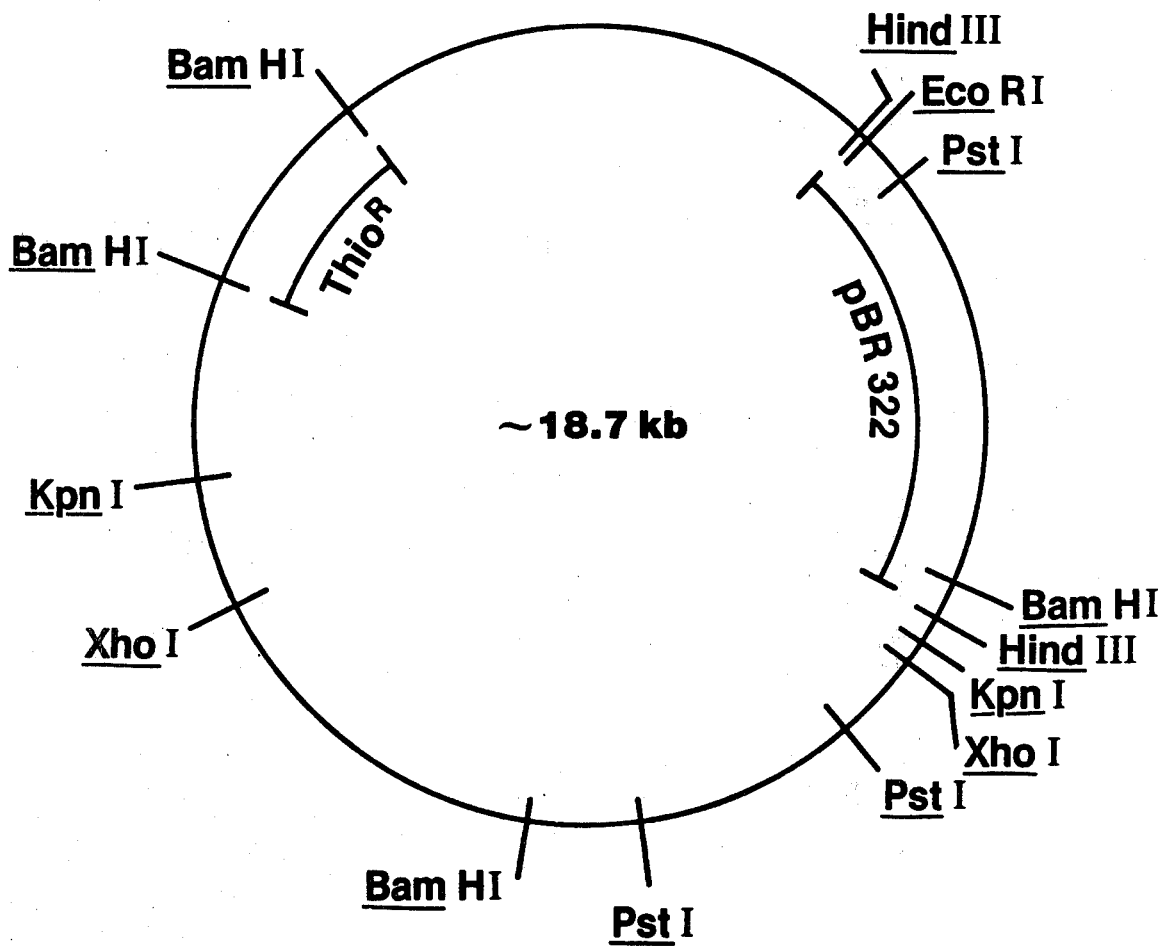
FIG. 3 is a restricton site map of plasmid pLR2.
Figure 4:
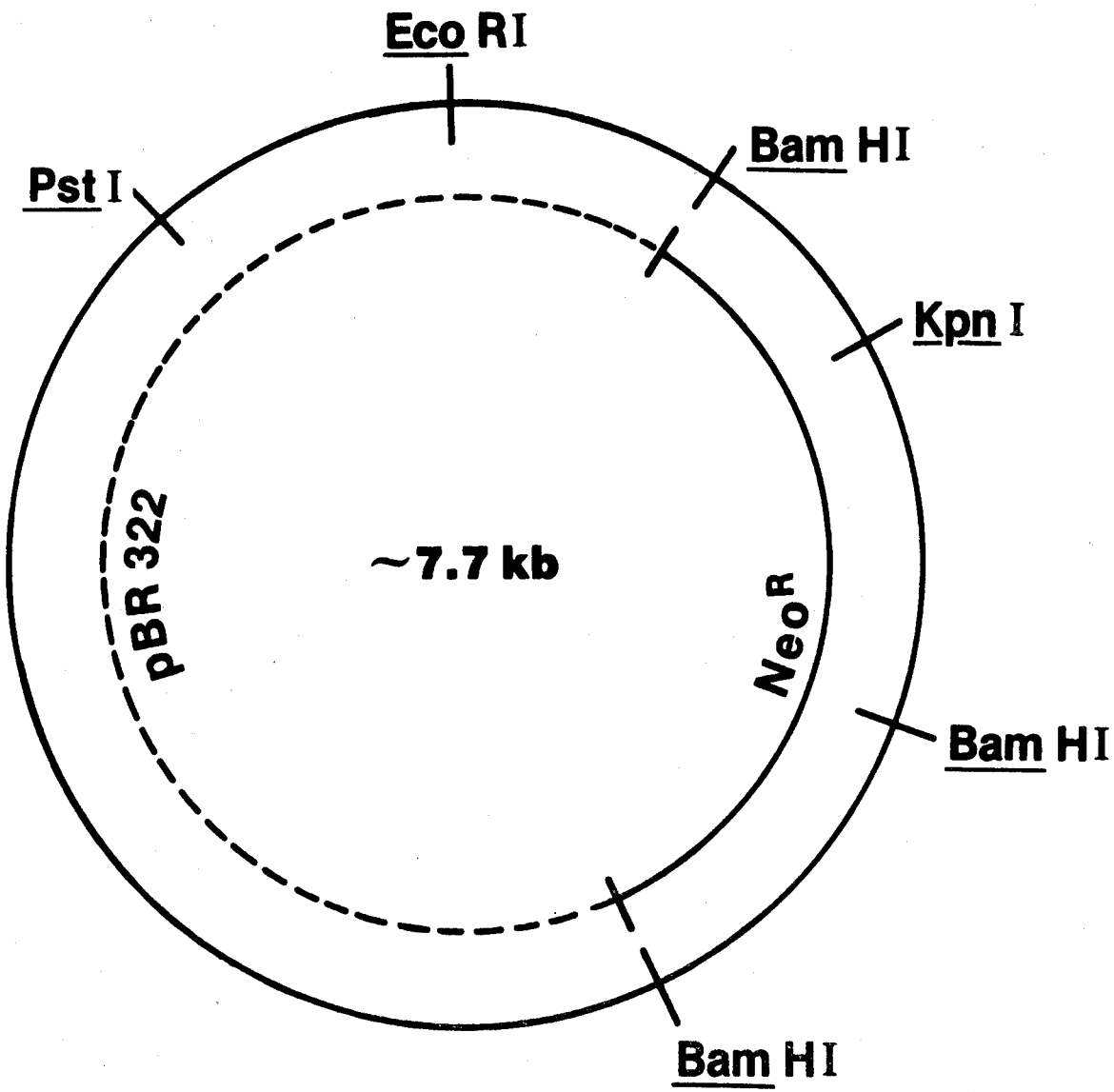
FIG. 4 is a restriction site map of plasmid pLR4.

The following examples further illustrate and detail the invention disclosed herein. Both an explanation of and the actual procedures for constructing the invention are described where appropriate.

EXAMPLE 1

Isolation of Plasmid pEL7

A. Culture of *Streptomyces ambofaciens*/pEL7

A vegetative inoculum of *Streptomyces ambofaciens*/pEL7 (NRRL 12523) was conventionally prepared by growing the strain under submerged aerobic conditions in 50 ml. of sterilized vegetative medium with the following preferred composition.

| Ingredient | Amount |
|---|---|
| Glucose | 20 g./l. |
| Nutrisoy flour* | 15 g./l. |
| Corn steep liquor* | 10 g./l. |
| CaCO$_3$ | 2 g./l. |

| Ingredient | Amount |
|---|---|
| Water (tap) | 11 l.1 l. |

*Nutrisoy flour is obtained from Archer Daniels Midland Company, 4666 Faries Parkway, Decatur, Illinois 62526.
*Corn steep liquor is obtained from CPC International, Corn Products, P.O. Box 3000, Englewood, N.J. 07632.

The vegetative inoculum was incubated for 48 hours at a temperature of 30° C. and a pH of 6.5. After incubation, about 1.0 ml. of the inoculum was transferred to 50 ml. of sterilized cell production medium with the following preferred composition.

| Ingredient | Amount |
|---|---|
| Trypticase soy broth* | 30 g./l. |
| Glucose | 5 g./l. |
| Glycine | 5 g./l. |
| Deionized water | 1 g./l. |

*Trypticase soy broth is obtained from Difco Laboratories, Detroit, Michigan.

The inoculated cell production medium was incubated for about 20 hours at 30° C. The pH was not adjusted. After incubation, the *Streptomyces ambofaciens*/pEL7 cells were ready for harvest and subsequent isolation of plasmid DNA.

B. Plasmid Isolation

About 10 g. (wet wgt) of *Streptomyces ambofaciens*/pEL7 cells were harvested by centrifugation (10 minutes, 5° C., 10,000 rpm). The cells were homogenized using a tissue grinder, washed in TES buffer (0.05 M tris(hydroxymethyl)aminomethane [tris], 0.005 M EDTA, and 0.05 M NaCl, pH 8.0), and then suspended in TES buffer containing 25% sucrose. After the addition of about 120 mg. of lysozyme in 20 ml. of TES-25% sucrose buffer, the suspension was incubated at 35°–37° C. for about 20 minutes and, upon addition of 40 ml. of 0.25 M EDTA, pH 8.0, the suspension was again incubated at 35° C. for 10 minutes. Following this, about 40 ml. of 5% SDS (sodium dodecyl sulfate) in TE buffer (0.01 M tris, 0.001 M EDTA, pH 8.0) was added and then, after the resultant mixture was again incubated at 35°–37° C. for 20 minutes, about 50 ml. of 5 M NaCl in deionized water was added. The mixture was stirred, placed on an ice bath for about 4 hours, and then centrifuged (30 minutes, 4° C., 10,000 rpm). About 0.313 volumes of 42% polyethylene glycol in deionized water were added to the NaCl supernatant and the resulting mixture was cooled at 4° C. for about 18 hours. The DNA precipitate was collected by centrifugation (5 minutes, 4° C., 3000 rpm) and was then dissolved in TES buffer at pH 8.0. Centrifugation (40 hours, 15° C., 35,000 rpm) using cesium chloride and ethidium chloride gradients separated the DNA into two well defined bands with the lower band constituting the desired plasmid pEL7. Following conventional procedures, the plasmid band was removed, washed twice with isoamyl alcohol, dialyzed over TE buffer at pH 8.0, and precipitated with ethanol. The thus isolated plasmid pEL7 DNA was dissolved in 0.4 ml. of TE buffer at pH 8.0, and was then frozen at −20° C. for storage.

EXAMPLE 2

Construction of Plasmid pLR2

A. HindIII Digestion of Plasmid pIJ6

About 20 μl. (20 μg.) of plasmid pIJ6 DNA, disclosed in Thompson et al., 1980, Nature 286:525, 5 μl. BSA (Bovine serum albumin, 1 mg./ml.), 19 μl. water, 1 μl. of Hind III (containing 3 new England Bio Lab Units) restriction enzyme*, and 5 μl. reaction mix** were incubated at 37° C. for 2 hours. The reaction was terminated by the addition of about 50 μl. of 4 M ammonium acetate and 200 μl. of 95% ethanol. The resultant DNA precipitate was washed twice in 70% ethanol, dried in vacuo, suspended in 20 μl. of TE buffer, and frozen at −20° C. for storage.

*Restriction enzymes can be obtained from the following sources:
New England Bio Labs., Inc.
32 Tozer Rd.
Beverly, Massachusetts 01915
Boehringer-Mannheim Biochemicals
7941 Castleway Dr.
Indianapolis, Indiana 46250
**Reaction mix for HindIII restriction enzyme was prepared with the following composition.
600 mM NaCl
100 mM Tris-HCl, pH 7.9
70 mM MgCl$_2$
10 mM Dithiothreitol

B. HindIII Digestion of Plasmid pBR322

About 8 μl. (4 μg.) of plasmid pBR322 DNA, 5 μl. reaction mix, 5 μl. BSA (1 mg./ml.), 31 μl. water, and 1 μl. of HindIII restriction enzyme were incubated at 37° C. for 2 hours. After the reaction was terminated by incubating at 60° C. for 10 minutes, about 50 μl. of ammonium acetate and 200 μl. of 95% ethanol were added. The resultant DNA precipitate was washed twice in 70% ethanol, dried in vacuo, and suspended in 45 μl. of water.

C. Ligation of HindIII Digested Plasmids pIJ6 and pBR322

About 20 μl. of HindIII treated plasmid pIJ6 (from Example 2A), 20 μl. of HindIII treated plasmid pBR322 (from Example 2B), 5 μl. BSA (1 mg./ml.), 1 μl. of T4DNA ligase*, and 5 μl. ligation mix** were incubated at 16° C. for 4 hours. The reaction was terminated by the addition of about 50 μl. 4 M ammonium acetate and 200 l. of 95% ethanol. The resultant DNA precipitate was washed twice in 70% ethanol, dried in vacuo, and suspended in TE buffer. The suspended DNA constituted the desired plasmid pLR2.

*T4 DNA ligase can be obtained from the following source:
New England Bio Labs., Inc.
32 Tozer Rd.
Beverly, Massachusetts 01915
**Ligation mix was prepared with the following composition:
500 mM Tris-HCl, pH 7.8
200 mM Dithiothreitol
100 mM MgCl$_2$
10 mM ATP

EXAMPLE 3

Construction of E. coli K12 HB101/pLR2

About 10 ml. of frozen competent E. coli K12 HB101 cells (Bolivar et al., 1977, Gene 2:75-93) were pelleted by centrifugation and then suspended in about 10 ml. of 0.01 M sodium chloride. Next, the cells were pelleted again, resuspended in about 10 ml. of 0.03 M calcium chloride solution, incubated on ice for 20 minutes, pelleted a third time, and finally, resuspended in 1.25 ml. of 0.03 M calcium chloride solution. The resultant cell suspension was competent for subsequent transformation.

Plasmid pLR2 in TE buffer (prepared in Example 2C) was ethanol precipitated, suspended in 150 µl. of 30 mM calcium chloride solution, and gently mixed in a test tube with about 200 µl. of competent E. coli K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 µg./ml. of ampicillin was added. The mixture was incubated with shaking at 37° C. for 1 hour and then placed on L-agar (Miller, 1972, Experiments in Molecular Genetics, Cold Spring Harbor Labs, Cold Spring Harbor, New York) containing ampicillin. Surviving colonies were selected and tested for the expected phenotype ($Amp^R$, $Tet^S$,) and constituted the desired E. coli K12 HB101/pLR2 transformants.

EXAMPLE 4

Construction of Plasmid pLR1

Plasmid pLR1 was prepared in substantial accordance with the teaching of Example 2A-C except that plasmid pIJ2, disclosed in Thompson et al., 1980, Nature 286:525, was used in place of plasmid pIJ6. The desired plasmid pLR1 was suspended in TE buffer.

EXAMPLE 5

Construction of E. coli K12 HB101/pLR1

The desired construction was carried out in substantial accordance with the teaching of Example 3 except that plasmid pLR1, rather than plasmid pLR2, was used for transformation. Surviving colonies were selected and tested for the expected phenotype ($Amp^R$, $Tet^S$,) and constituted the desired E. coli K12 HB101/pLR1 transformants.

EXAMPLE 6

Construction of Plasmid pLR4

A. Partial Bam HI Digestion of Plasmid pLR1

About 10 µl. (10 µg.) of plasmid pLR1, 5 µl. BSA (1 mg./ml.), 29 µl. water, 1 µl. of BamHI (diluted 1:4 with water) restriction enzyme, and 5 µl. reaction mix* were incubated at 37° C. for 15 minutes. The reaction was terminated by the addition of about 50 µl. of 4 M ammonium acetate and 200 µl. of 95% ethanol. The resultant DNA precipitate was washed twice in 70% ethanol, dried in vacuo, and suspended in 20 µl. water.

---

*Reaction mix for BamHI restriction enzyme was prepared with the following composition.
1.5 M NaCl
60 mM Tris-HCl, pH 7.9
60 mM $MgCl_2$

BamHI Digestion of Plasmid pBR322

The desired digestion was carried out in substantial accordance with the teaching of Example 2B except that BamHI restriction enzyme was used in place of HindIII restriction enzyme. The digested plasmid pBR322 was suspended in 29 µl. of water.

C. Ligation of Partial BamHI Digested Plasmid pLR1 and BamHI Digested Plasmid pBR322

The desired ligation was carried out in substantial accordance with the teaching of Example 2C. The resultant ligated DNA was suspended in TE buffer and constituted the desired plasmid pLR4.

EXAMPLE 7

Construction of E. coli K12 HB101/pLR4

The desired construction was carried out in substantial accordance with the teaching of Example 3 except that plasmid pLR4, rather than plasmid pLR2, was used for transformation. Surviving colonies were selected and tested for the expected phenotype ($Amp^R$, $Tet^S$,) and constituted the desired E. coli K12 HB101/pLR4 transformants.

EXAMPLE 8

Construction of Plasmids pEL7.1 and pEL7.2

A. BamHI Digestion of Plasmid pLR2 and Isolation of the 1.6 kb Thiostrepton Resistance Conferring Fragment About 50 µg. of plasmid pLR2 DNA, 20 µl. reaction mix, 10 µl. 0.1 M dithiothretiol, 20 µl. BSA (1 mg./ml.), 100 µl. water, and 5 µl. (4 units/µl.) of BamHI restriction enzyme were incubated at 37° C. for 2 hours. After adding an equal volume of 4 M ammonium acetate and 2 volumes of 95% ethanol, the mixture was cooled at −20° C. for about 18 hours to precipitate the DNA. The DNA precipitate was collected by centrifugation and then suspended in about 50 µl. of TE buffer. The desired 1.6 kb BamHI restriction fragment was isolated conventionally from the DNA suspension by gel electrophoresis. Following isolation, the fragment was resuspended in about 20 µl. of TE buffer for subsequent ligation.

B. BamHI Digestion of Plasmid pEL 7

The desired digestion was carried out in substantial accordance with the teaching of Example 8A except that plasmid pEL7, rather than plasmid pLR2, was used. In addition, the DNA digest was not electrophoresed but was suspended directly in 20 µl. of TE buffer for subsequent ligation.

C. Ligation

A mixture of about 20 µg. of BamHI restricted plasmid pEL7 DNA, 10 µg. of the 1.6 kb BamHI restriction fragment of plasmid pLR2, 5 µl. BSA (1 mg./ml.), 10 µl. ligation mix, 45 µl. water, and 3.5 µl. of T4 DNA ligase were incubated at about 16° C. for about 18 hours. After adding 0.1 volume of 3 M ammonium acetate and 2 volumes of cold ethanol, the mixture was cooled to −20° C. for about 18 hours to precipitate the DNA.

The DNa precipitate was collected by centrifugation, washed with 70% ethanol, collected again, and then suspended in 50 μl. of medium P (Hopwood and Wright, 1978, J. Molecular and General Genetics 162:307) for subsequent transformation.

Figure 5:
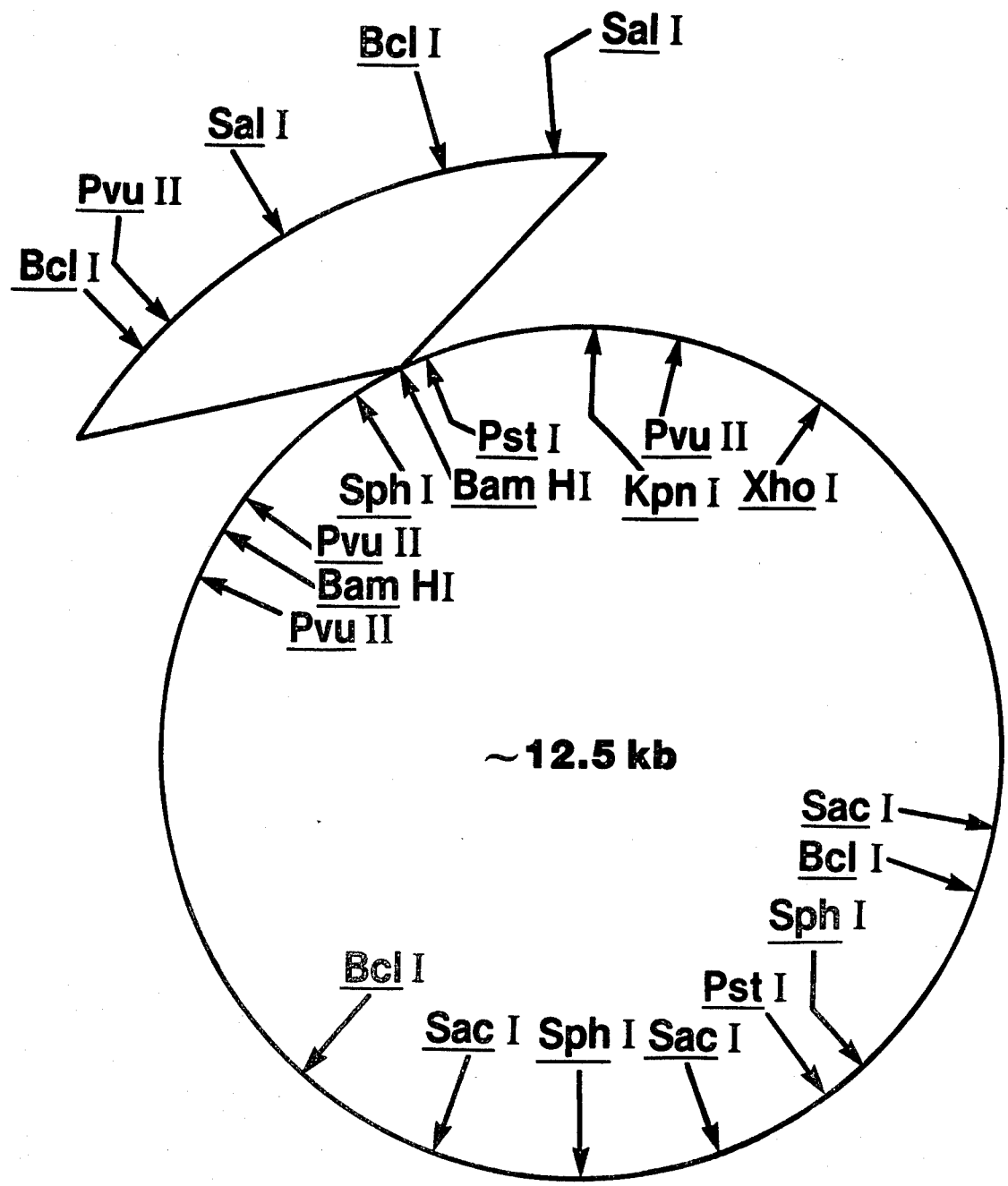
FIG. 5 is a restriction site map of plasmid pEL7.1.
Figure 6:
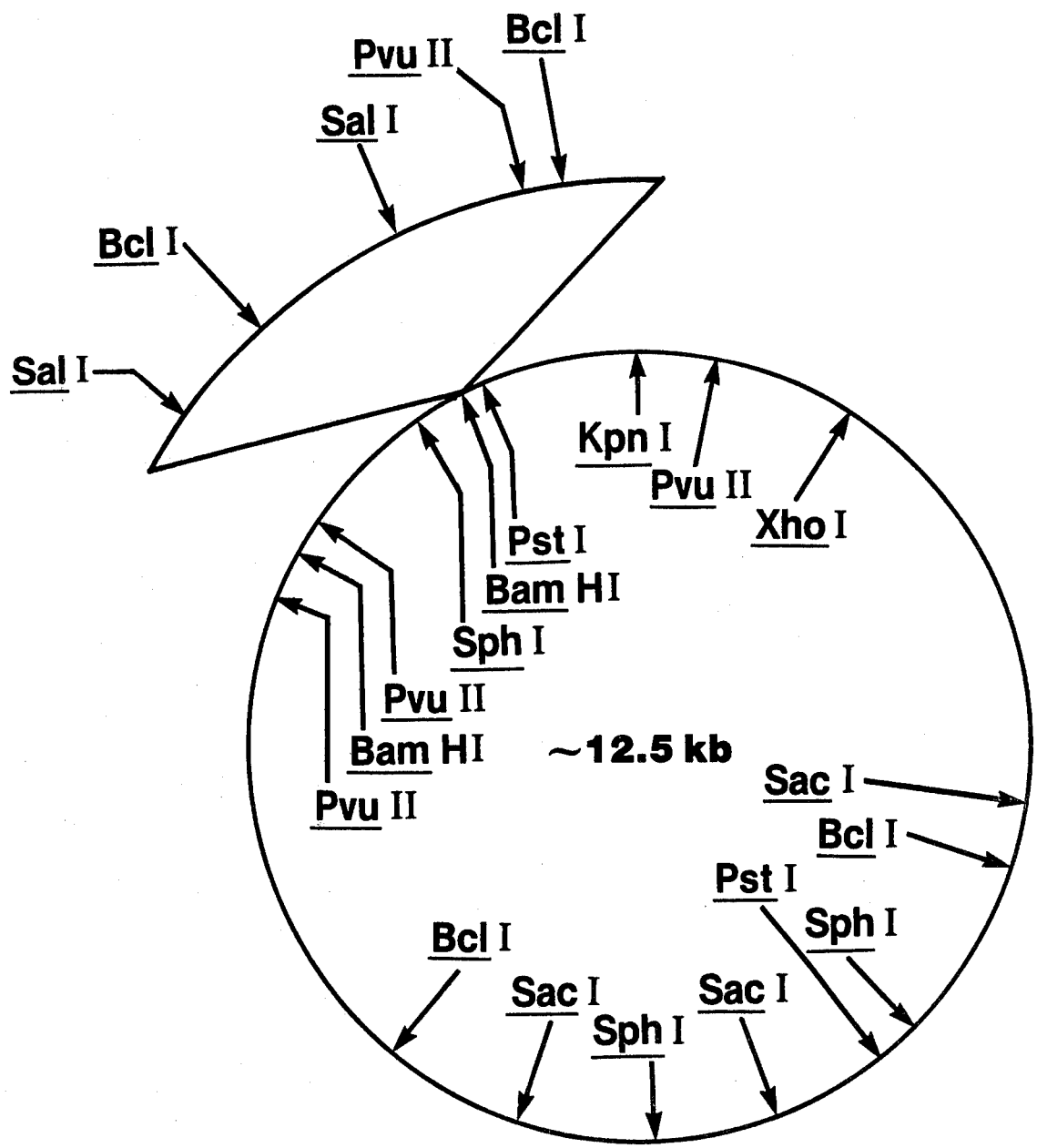
FIG. 6 is a restriction site map of plasmid pEL7.2.

Recombinant plasmids of two orientations result depending upon the orientation of the inserted 1.6 kb BamHI thiostrepton resistance conferring fragment. In addition plasmid pEL7 is also restored by self ligation. Plasmid pEL7.1 designates the resultant recombinant plasmid in which the PvuII restriction site of the resistance conferring fragment is inserted closest to the flanking SphI site of plasmid pEL7. Plasmid pEL7.2 designates the recombinant plasmid with the reverse orientation. Thus, the final DNA suspension contains plasmids which include plasmids pEL7, pEL7.1, and pEL7.2. In addition, the insertional isomers of plasmids pEL7.1 and pEL7.2 are also produced since plasmid pEL7 has two BamHI restriction sites for the insertion of the thiostrepton resistance fragment. A restriction site and functional map of each of plasmids pEL7.1 and pEL7.2 is respectively presented in FIGS. 5 and 6 of the accompanying drawings.

EXAMPLE 9

Construction of *Streptomyces ambofaciens*/pEL7, pEL7.1 and *Streptomyces ambofaciens*/pEL7, pEL7.2

Using about 20 μg. DNA from Example 8C and $1 \times 10^8$ protoplasts of *Streptomyces ambofaciens*, a strain deposited and made part of the stock culture collection of the Northern Regional Research Laboratory, Peoria, Illinois, from which it is available to the public under the accession number NRRl 2420, the desired constructions were carried out in substantial accordance with the teaching of International Publication (of International Patent Application No. PCT/GB 79/00095) No. WO79/01169, Example 2. The desired transformants were selected for thiostrepton resistance by plating on Bennett's Modified Medium* containing about 50 μg./ml. of antibiotic thiostrepton. The resultant *Streptomyces ambofaciens*/pEL7, pEL7.1 and *S. ambofaciens*/- pEL7, pEL7.2 thiostrepton resistant colonies were isolated, cultured, and then conventionally identified by restriction enzyme and gel electrophoretic analysis of the constitutive plasmids.

*Bennett's medium (Agar), disclosed in Waksman, 1961, The Actinomycetes, Volume II, The Williams and Wilkins Company, Baltimore, Maryland, was modified by adding CoCl₂.H₂O (0.01 g./L.) and by replacing glucose with dextrin.

EXAMPLE 10

Construction of Plasmids pEL7.3 and pEL7.4

A. PstI Digestion of Plasmid pLR1 and Isolation of the 3.5 kb Neomycin Resistance Conferring Fragment About 50 μg. of plasmid pLR1 DNA, 20 μl. reaction mix*, 10 μl. 0.1 M dithiothretiol, 20 μl. BSA (1 mg./ml.), 100 μl. water, and 5 μl. (4 units/ul.) of PstI restriction enzyme* were incubated at 37° C. for 2 hours. After adding an equal volume of 4 M ammonium acetate and 2 volumes of 95% ethanol, the mixture was cooled at −20° C. for about 18 hours to precipitate the DNA. The DNA precipitate was collected by centrifugation and then suspended in about 50 μl. of TE buffer. The desired 3.5 kb PstI restriction fragment was isolated conventionally from the DNA suspension by gel electrophoresis. Following isolation, the fragment was resuspended in about 20 μl. of TE buffer for subsequent ligation.

---

*Reaction mix for PstI restriction enzyme was prepared with the following composition.
 50 mM NaCl
 6 mM Tris-HCl, pH 7.4
 6 mM MgCl₂
 6 mM 2-mercaptoethanol
 100 μg./ml. BSA
**Restriction enzymes can be obtained from the sources listed in Example 2.

---

B. PstI Digestion of Plasmid pEL7

The desired digestion was carried out in substantial accordance with the teaching of Example 10A except that plasmid pEL7, rather than plasmid pLR1, was used. In addition, the DNA digest was not electrophoresed but was suspended directly in 20 μl. of TE buffer for subsequent ligation.

C. Ligation

The desired ligation is carried out by reacting about 20 μg. of PstI restricted plasmid pEL7 DNA and about 19 μg. of the 3.5 kb PstI restriction fragment of plasmid pLR1 in substantial accordance with the teaching of Example 8C.

Figure 7:
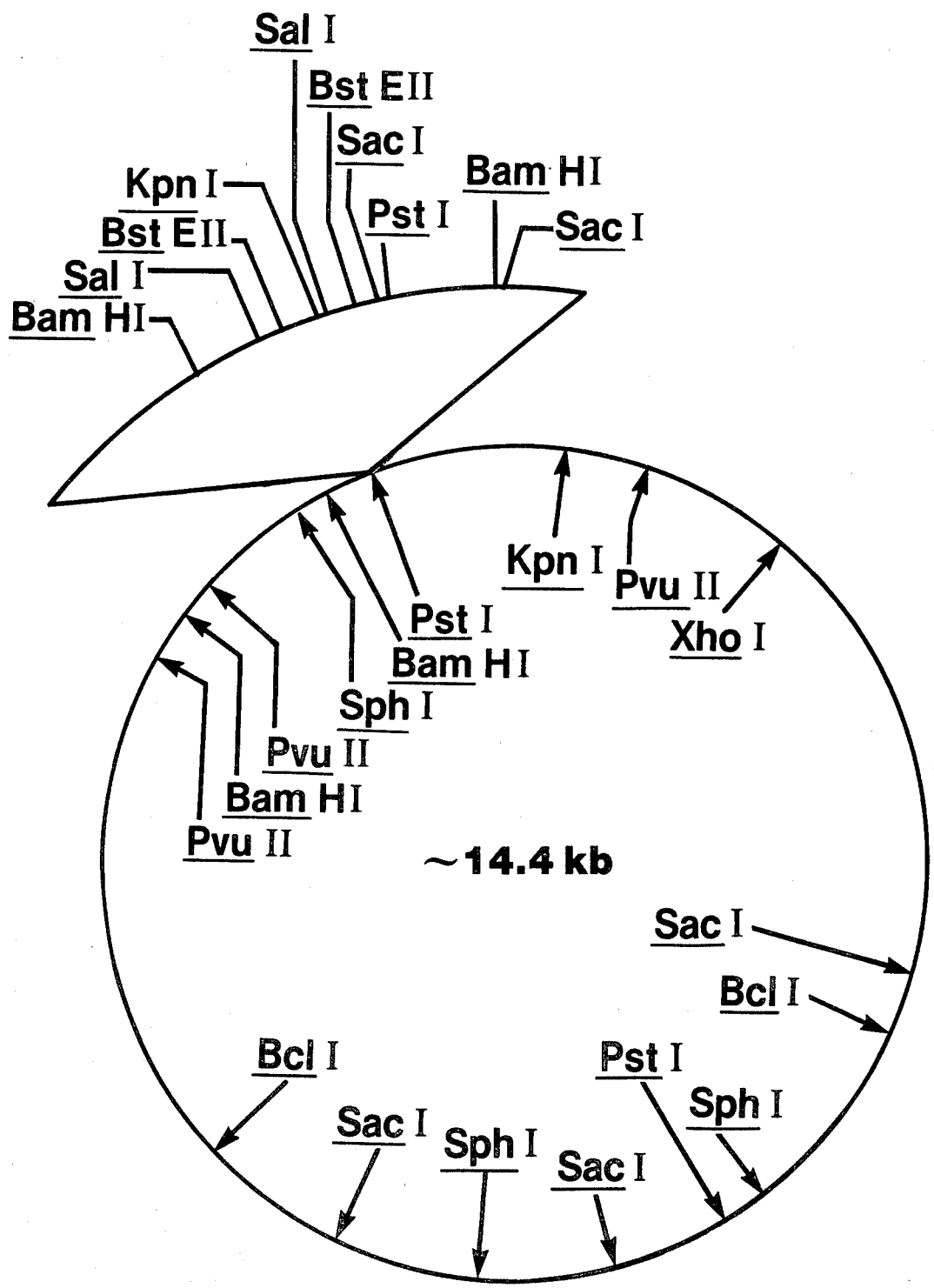
FIG. 7 is a restriction site map of plasmid pEL7.3.
Figure 8:
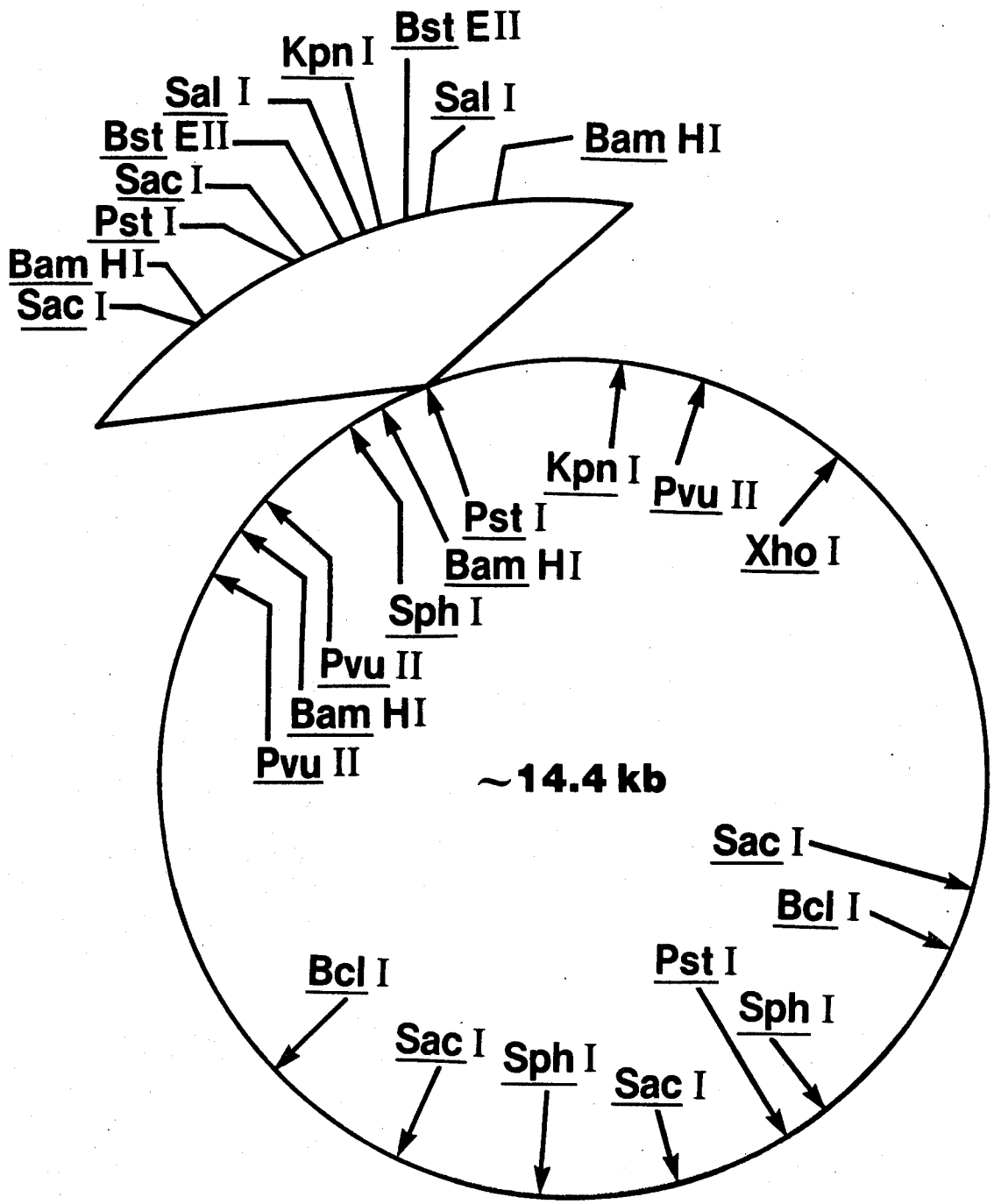
FIG. 8 is a restriction site map of plasmid pEL7.4.

Recombinant plasmids of two orientations result depending upon the orientation of the inserted 3.5 kb PstI neomycin resistance conferring fragment. In addition, plasmid pEL7 is also restored by self ligation. Plasmid pEL7.3 designates the recombinant plasmid in which the SacI restriction site of the resistance conferring fragment is inserted closest to the flanking KpnI site of plasmid pEL7. Plasmid pEL7.4 designates the recombinant plasmid with the reverse orientation. Thus, the final DNA suspension contains plasmids which include plasmids pEL7, pEL7.3, and pEL7.4. In addition, the insertional isomers of plasmids pEL7.3 and pEL7.4 are also produced since plasmid pEL7 has two PstI restriction sites for the insertion of the neomycin resistance fragment. A restriction site and functional map of each of plasmids pEL7.3 and pEL7.4 is respectively presented in FIGS. 7 and 8 of the accompanying drawings.

EXAMPLE 11

Construction of *Streptomyces ambofaciens*/pEL7, pEL7.3 and *Streptomyces ambofaciens*/pEL7, pEL 7.4

Using about 20 μg. DNA from Example 10C and $1 \times 10^8$ protoplasts of *Streptomyces ambofaciens*, (NRRL No. 2420), the desired constructions are carried out in substantial accordance with the teaching of International Publication (of International Patent Application No. PCT/GB 79/00095) No. WO79/01169, Example 2. The desired transformants are selected for neomycin resistance by plating on Bennett's Modified Medium containing about 1 μg./ml. of antibiotic neomycin*. The resultant *Streptomyces ambofaciens*/pEL7, pEL7.3 and *S. ambofaciens* pEL7, pEL7.4 neomycin resistant colonies are isolated, cultured, and then conventionally identified by restriction enzyme and gel electrophoretic analysis of the constitutive plasmids.

*Antibiotic neomycin can be obtained from Sigma, St. Louis, Missouri.

EXAMPLE 12

Construction of Plasmids pEL7.5 and pEL7.6

A. Isolation of Plasmids pEL7 and pEL7.1

The desired plasmids are isolated from *Streptomyces ambofaciens*/pEL7, pEL7.1 (prepared in Example 9 and cultured according to the teaching of Example 1A) in substantial accordance with the isolation procedure of Example 1B. The thus isolated plasmid pEL7 and pEL7.1 DNA is suspended in TE buffer at pH8.0 for subsequent restriction enzyme digestion.

B. PstI Digestion of Plasmids pEL7 and pEL7.1

The desired digestion is carried out in substantial accordance with the teaching of Example 10A, except that a mixture of plasmid pEL7 and pEL7.1 DNA is used instead of plasmid pLR1 DNA. The thus digested DNA is suspended in 20 μl. of TE buffer for subsequent ligation with the 3.5 kb PstI restriction fragment of plasmid pLR1.

C. Ligation

The desired ligation is carried out by reacting about 20 μg. of the PstI restricted mixture of plasmid pEL7 and pEL7.1 DNA and about 10 μg. of the 3.5 kb PstI restriction fragment (prepared in Example 10A) in substantial accordance with the teaching of Example 10C.

A mixture of recombinant plasmids is produced since the 3.5 kb PstI fragments are ligated with either or both of plasmids pEL7 and pEL7.1. The recombinant plasmids, as previously described, are also of two orientations depending upon the orientation of the 3.5 kb PstI neomycin resistance conferring fragment. Thus, ligation with plasmid pEL7 results in plasmids pEL7.3 and pEL7.4 and ligation with plasmid pEL7.1 results in the desired plasmids pEL7.5 and pEL 7.6. In addition, plasmids pEL7 and pEL 7.1 are also restored by self ligation.

Figure 9:
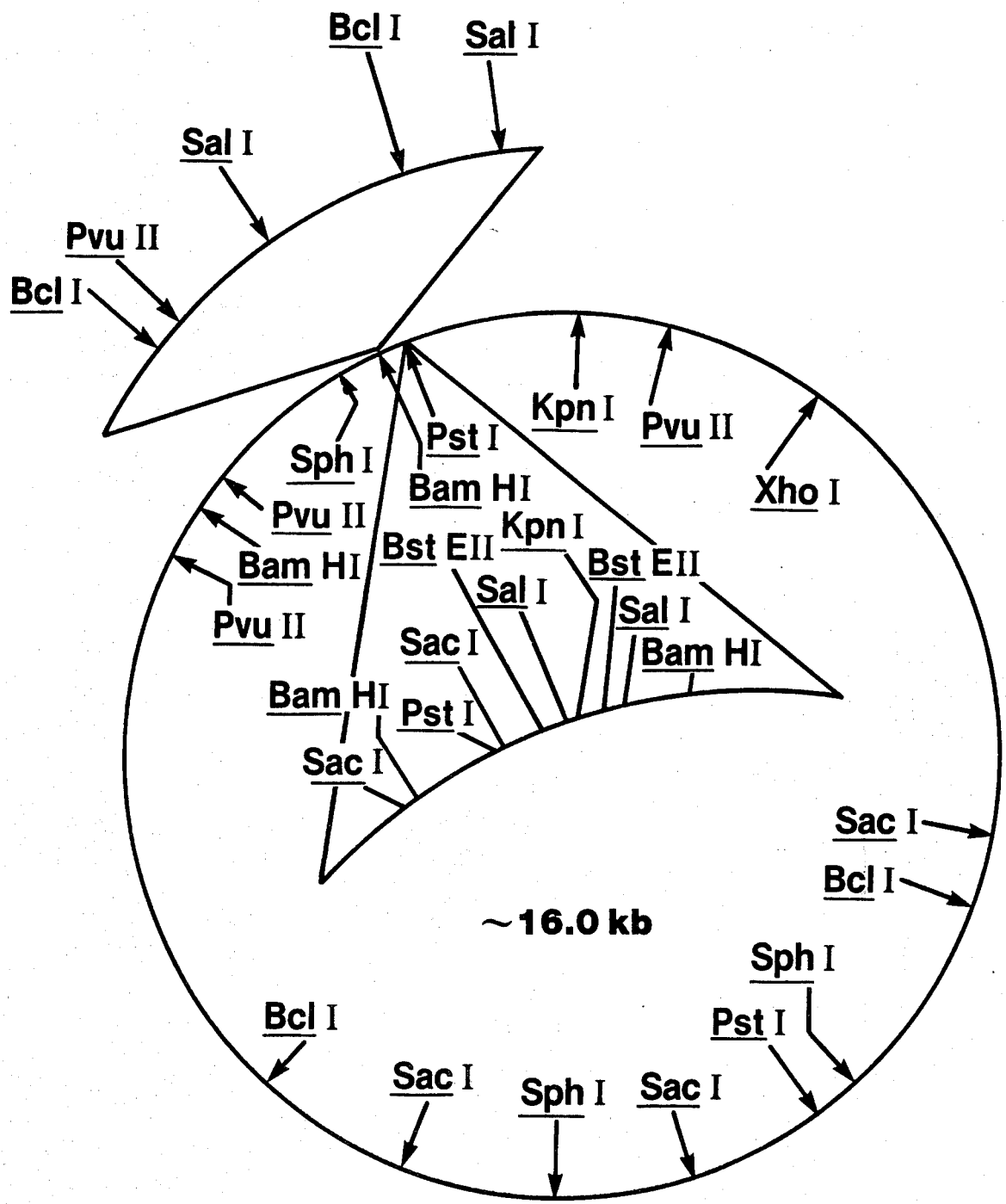
FIG. 9 is a restriction site map of plasmid pEL7.5.
Figure 10:
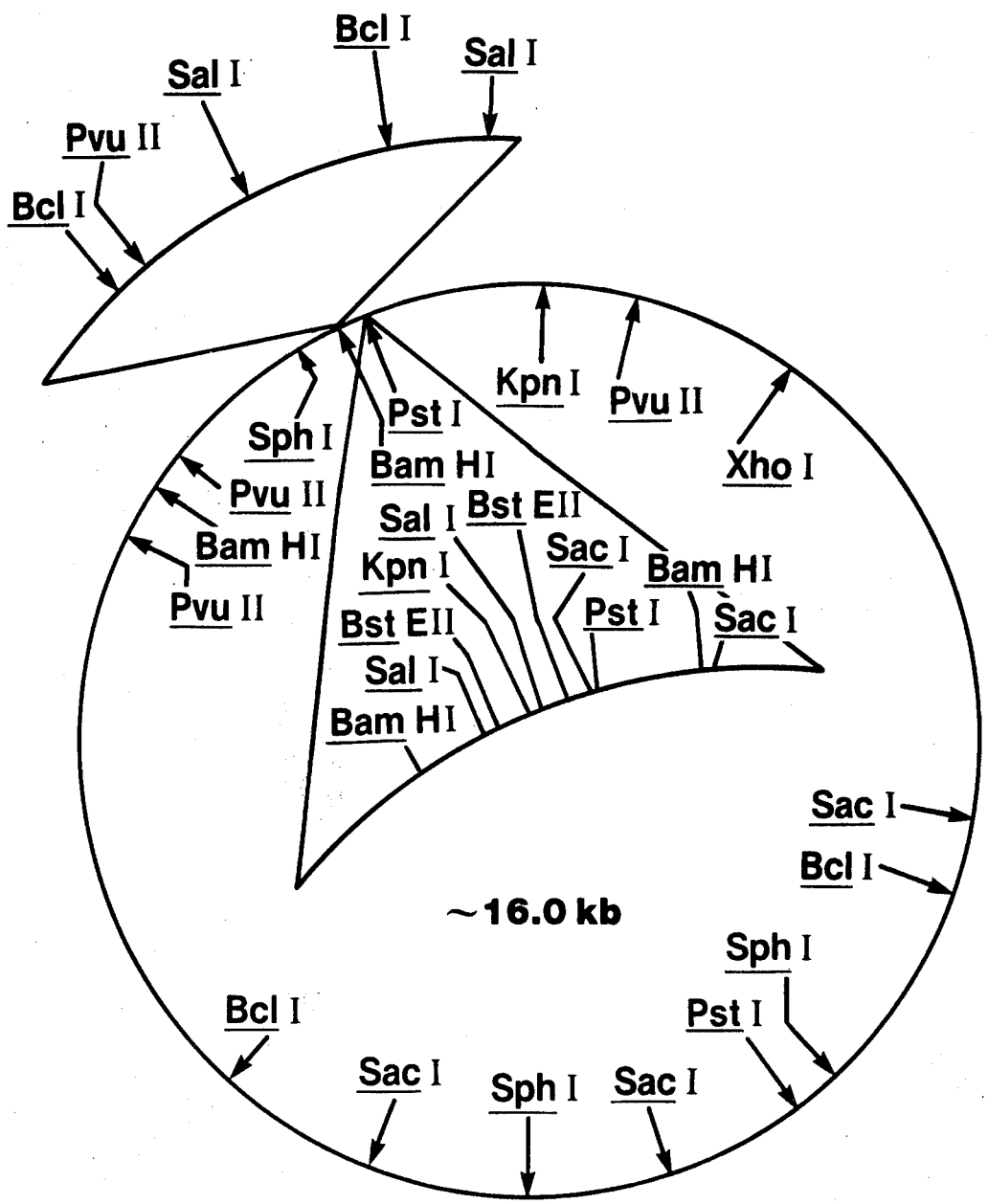
FIG. 10 is restriction site map of plasmid pEL7.6.

Plasmid pEL7.5 designates the recombinant plasmid in which the SacI restriction sites of the 3.5 Kb PstI neomycin resistance conferring fragment is inserted closest to the PvuII restriction site of the 1.6 kb BamHI thiostrepton resistance conferring fragment. Plasmid pEL7.6 designates the recombinant plasmid in which the 3.5 kb PstI neomycin resistance conferring fragment has the reverse orientation. Thus, the final DNA suspension contains plasmids which include plasmids pEL7, pEL7.1, pEL7.3, pEL7.4, pEL7.5, pEL7.6, and, for the reasons described in Examples 8 and 10, the insertional isomers of plasmids pEL7.3, pEL7.4, pEL7.5, and pEL7.6. A restriction site and functional map of each of the desired plasmids pEL7.5 and pEL7.6 is respectively presented in FIGS. 9 and 10 of the accompanying drawings.

EXAMPLE 13

Construction of *Streptomyces ambofaciens*/pEL7, pEL7.5 and *S. ambofaciens*/pEL7, pEL7.6

Using 20 μg. DNA from Example 12C and 1×10⁸ protoplasts of *Streptomyces ambofaciens*, (NRRL No. 2420), the desired constructions are carried out in substantial accordance with the teaching of International Publication (of International Patent Application No. PCT/GB 79/00095) No. WO79/01169, Example 2. The desired transformants are selected for thiostrepton and neomycin resistance by plating on Bennett's Modified Medium containing about 50 μg./ml. of antibiotic thiostrepton and 1 μg./ml. of antibiotic neomycin. The resultant *Streptomyces ambofaciens*/pEL7, pEL7.5 and *S. ambofaciens*/pEL7, pEL7.6 thiostrepton and neomycin resistant colonies are conventionally isolated, cultured, and then identified by restriction enzyme and gel electrophoretic analysis of the constitutive plasmids.

EXAMPLE 14

Construction of Plasmids pEL7.7 and pEL7.8

The desired plasmids are constructed in substantial accordance with the teaching of Example 12A–C, except that a mixture of plasmid pEL7 and pEL7.2 DNA (isolated from the *Streptomyces ambofaciens*/pEL7, pEL7.2 prepared in Example 9) is used instead of the mixture of plasmid pEL7 and pEL7.1 DNA.

A mixture of recombinant plasmids is produced since the 3.5 kb PstI fragments are ligated with either or both of plasmids pEL7 and pEL7.2. The recombinant plasmids, as previously described, are also of two orientations depending upon the orientation of the 3.5 kb PstI neomycin resistance conferring fragment. Thus, ligation with plasmid pEL7 results in plasmids pEL7.3 and pEL7.4 and ligation with plasmid pEL7.2 results in the desired plasmids pEL7.7 and pEL7.8. In addition, plasmids pEL7 and pEL7.2 are also restored by self ligation.

Figure 11:
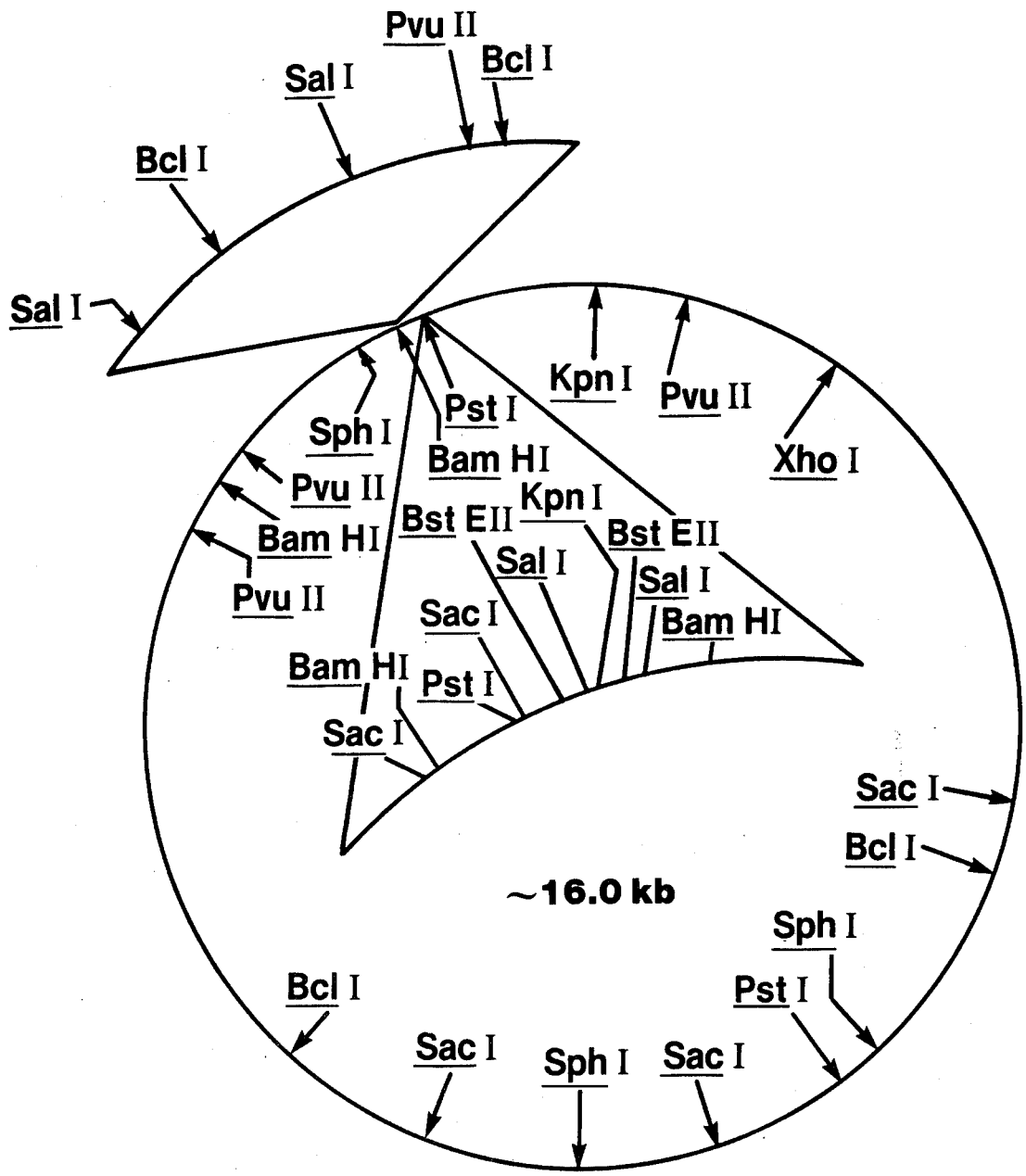
FIG. 11 is restriction site map of plasmid pEL7.7.
Figure 12:
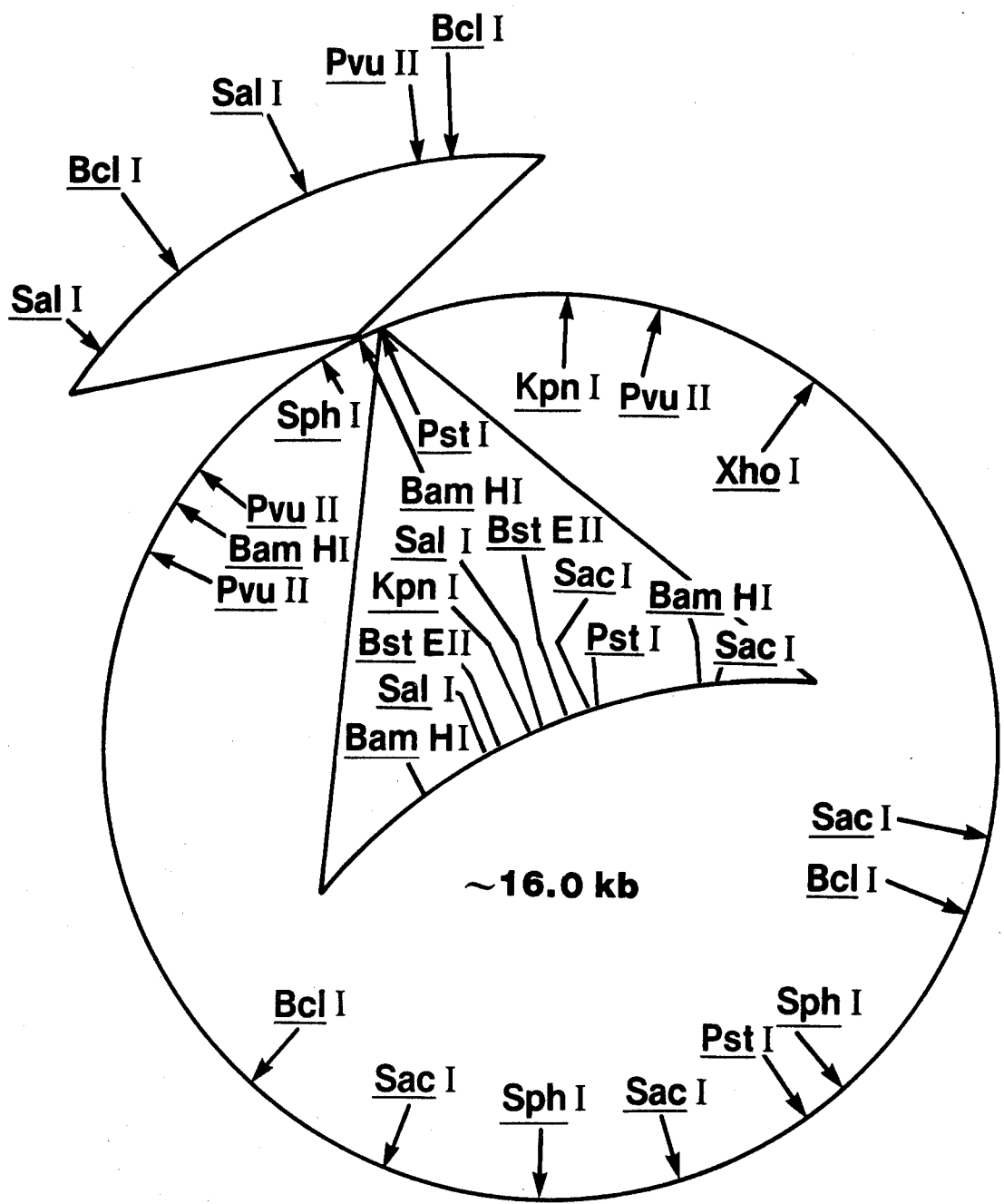
FIG. 12 is restriction site map of plasmid pEL7.8.

Plasmid pEL7.7 designates the recombinant plasmid in which the SalI (flanking BamHI) restriction site of the 3.5 kb PstI neomycin resistance conferring fragment is inserted farthest from the PvuII restriction site of the 1.6 kb BamHI thiostrepton resistance conferring fragment. Plasmid pEL7.8 designates the recombinant plasmid in which the 3.5 kb PstI neomycin resistance conferring fragment has the reverse orientation. Thus, the final DNA suspension contains plasmids which include plasmids pEL7, pEL7.2, pEL7.3, pEL7.4, pEL7.7, pEL7.8, and, for the reasons described in Examples 8 and 10, the insertional isomers of plasmids pEL7.3, pEL7.4, pEL7.7, and pEL7.8. A restriction site and functional map of each of the desired plasmids pEL7.7 and pEL7.8 is respectively presented in FIGS. 11 and 12 of the accompanying drawings.

EXAMPLE 15

Construction of *Streptomyces ambofaciens*/pEL7, pEL7.7 and *S. ambofaciens*/pEL7, pEL7.8

Using DNA prepared in Example 14, the desired transformants are constructed in substantial accordance with the procedure of Example 13. The resultant *Streptomyces ambofaciens*/pEL7, pEL7.7 and *S. ambofaciens*/pEL7, pEL7.8 thiostrepton and neomycin resistant colonies are conventionally isolated, cultured, and then identified by restriction enzyme and gel electrophoretic analysis of the constitutive plasmids.

EXAMPLE 16

Construction of Plasmid pLR5 and Plasmid pLR6

Figure 13:
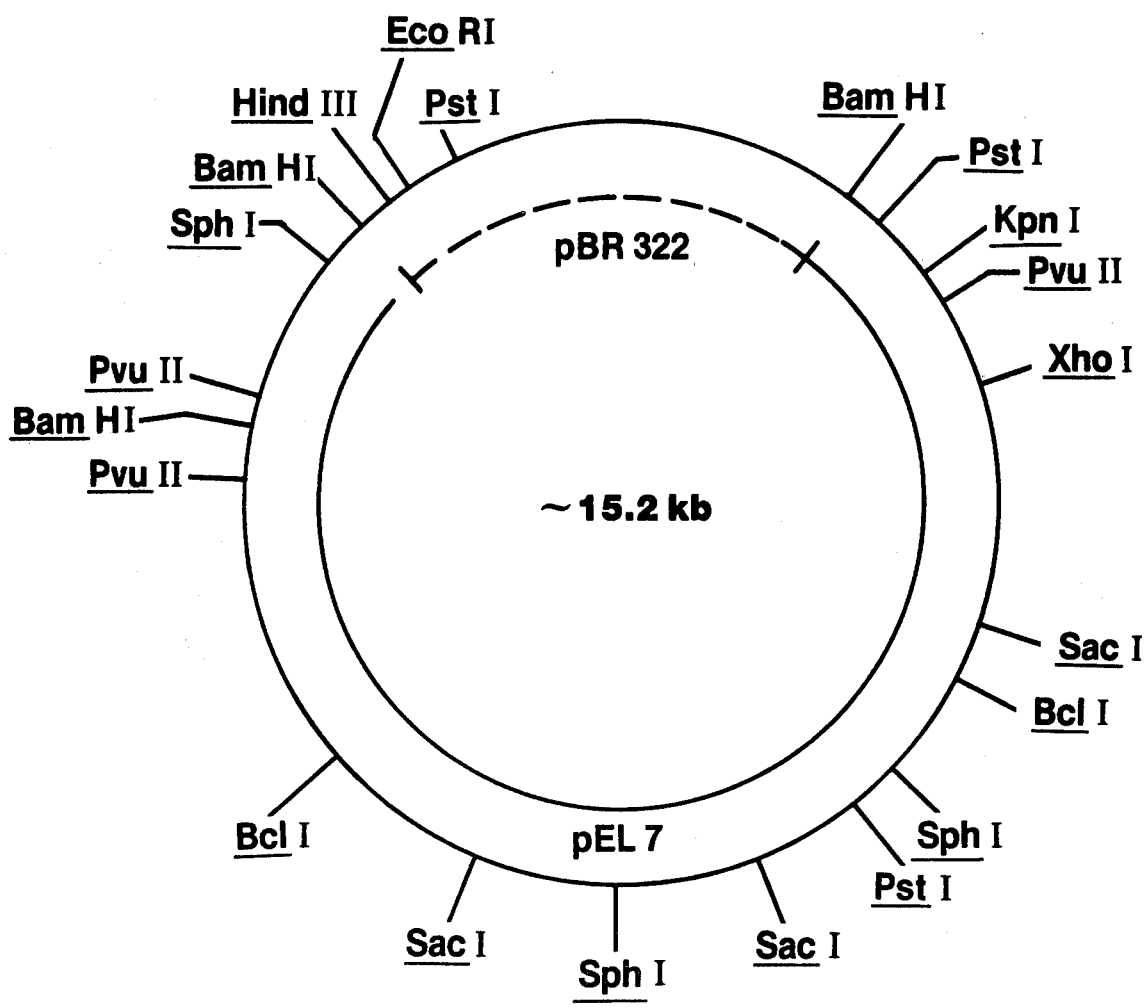
FIG. 13 is restriction site map of plasmid pLR5.
Figure 14:
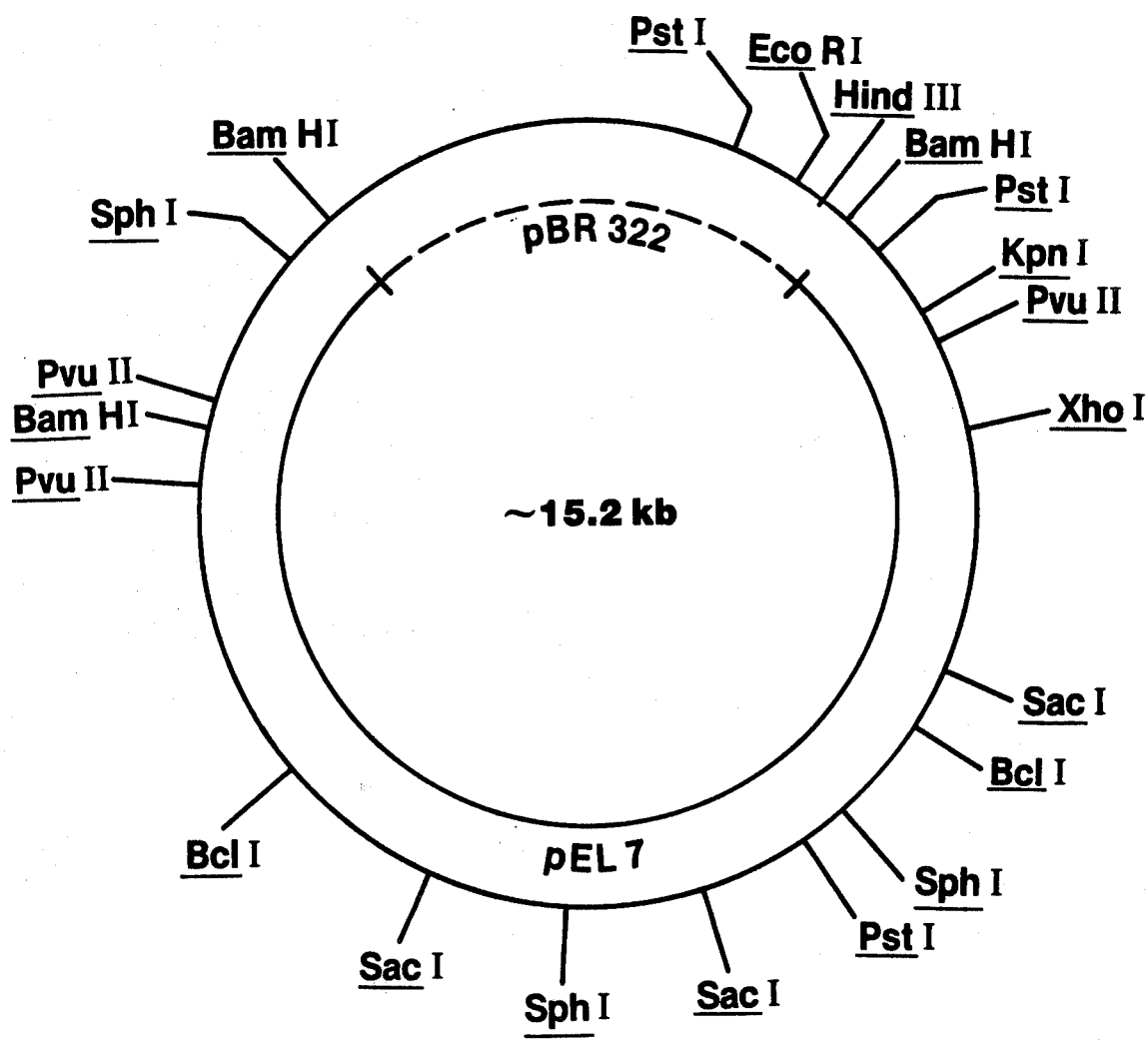
FIG. 14 is restriction site map of plasmid pLr6.

Plasmids pLR5 and pLR6 are prepared in substantial accordance with the teaching of Example 6A–C except that plasmid pEL7 is used in place of plasmid pLR1. Recombinant plasmids of two orientations result depending upon the orientation of the inserted plasmid pEL7 DNA. In addition, for the reasons described in Example 8, insertional isomers of plasmids pLR5 and pLR6 are also produced. A restriction site and functional map of each of plasmids pLR5 and pLR6 is presented in FIGS. 13 and 14 of the accompanying drawings.

EXAMPLE 17

Construction of *E. coli* K12 HB101/pLR5 and *E. coli* K12 HB101/pLR6

The desired construction is carried out in substantial accordance with the teaching of Example 3 except that plasmids pLR5 and pLR6 (from Example 16), rather than plasmid pLR2, are used for transformation. Surviving colonies are selected and tested for the expected phenotype (Amp$^R$, Tet$^S$) and constitute the desired *E. coli* K12 HB101/pLR5 and *E. coli* K12 HB101/pLR6 transformants. The resistant transformant colonies are isolated, cultured according to known procedures, and then conventionally identified by restriction enzyme and gel electrophoretic analysis of the constitutive plasmids.

EXAMPLE 18

Construction of *Streptomyces ambofaciens*/pEL7, pLR5

Plasmid pLR5 is conventionally isolated from *E. coli* K12 HB101/pLR5 (prepared in Example 17) and then transformed into *Streptomyces ambofaciens*/pEL7 in substantial accordance with the teaching of Example 13. Colonies are selected and the desired *Streptomyces ambofaciens*/pLR5 transformants identified by restriction enzyme and gel electrophoretic analysis of the constituent plasmids.

Representative plasmids that can be constructed according to the foregoing teaching include the following listed below.

Plasmid names designate and also encompass all the insertional and orientational isomers resulting from a particular construction.

| Plasmid Name | Construction |
| --- | --- |
| pLR7 | pBR322 and pEL7.1 |
| pLR8 | pBR322 and pEL7.2 |
| pLR9 | pBR322 and pEL7.3 |
| pLR10 | pBR322 and pEL7.4 |
| pLR11 | pBR322 and pEL7.5 |
| pLR12 | pBR322 and pEL7.6 |
| pLR13 | pBR322 and pEL7.7 |
| pLR14 | pBR322 and pEL7.8 |

Representative transformants of plasmids pLR7 through pLR14 include the following listed below.

*E. coli* K12 HB101/pLR7
*E. coli* K12 HB101/pLR8
*E. coli* K12 HB101/pLR9
*E. coli* K12 HB101/pLR10
*E. coli* K12 HB101/pLR11
*E. coli* K12 HB101/pLR12
*E. coli* K12 HB101/pLR13
*E. coli* K12 HB101/pLR14
*Streptomyces ambofaciens*/pEL7, pLR7
*Streptomyces ambofaciens*/pEL7, pLR9
*Streptomyces ambofaciens*/pEL7, pLR11

We claim:

1. A novel pair of recombinant DNA cloning vectors, said pair comprising:
   (a) novel plasmid pEL7, and
   (b) a second plasmid that is functionally dependent upon plasmid pEL7, said second plasmid comprising a restriction fragment of plasmid pEL7 and one or more different DNA segments that convey resistance to at least one antibiotic when transformed into a sensitive host cell, said host cell being susceptible to transformation, cell division, and culture.

2. The vector pair of claim 1 wherein the one or more DNA segments in the second plasmid that convey antibiotic resistance are selected from the group of segments that convey resistance to either or both of antibiotics thiostrepton and neomycin.

3. The vector pair of claim 2 wherein the DNA segment in the second plasmid conveys resistance to antibiotic thiostrepton.

4. The vector pair of claim 3 wherein the DNA segment is the 1.6 kb BamHI restriction fragment of plasmid pLR2.

5. The vector pair of claim 3 wherein the DNA segment is the 13 kb PstI restriction fragment of plasmid pLR2.

6. The vector pair of claim 2 wherein the DNA segment in the second plasmid conveys resistance to antibiotic neomycin.

7. The vector pair of claim 6 wherein the DNA segment is the 3.5 kb PstI restriction fragment of plasmid pLR1.

8. The vector pair of claim 6 wherein the DNA segment is the 3.4 kb BamHI restriction fragment of plasmid pLR1 or plasmid pLR4.

9. The vector pair of claim 2 wherein the DNA segments are the 1.6 kb BamHI restriction fragment of plasmid pLR2 and the 3.4 kb BamHI restriction fragment of plasmids pLR1 or pLR4.

10. The vector pair of claim 2 wherein the DNA segments are the 1.6 kb BamHI restriction fragment of plasmids pLR2 and the 3.5 kb PstI restriction fragment of plasmid pLR1.

11. The vector pair of claim 2 wherein the DNA segments are the 13 kb PstI restriction fragment of plasmid pLR2 and the 3.5 kb PstI restriction fragment of plasmids pLR1.

12. A single recombinant DNA cloning vector comprising the novel plasmid pEL7 of claim 1.

13. A recombinant DNA cloning vector selected from the group consisting of plasmids pLR1, pLR2, and pLR4.

14. The recombinant DNA cloning vector of claim 13 which is plasmid pLR1.

15. The recombinant DNA cloning vector of claim 13 which is plasmid pLR2.

16. The recombinant DNA cloning vector of claim 13 which is plasmid pLR4.

17. A novel recombinant DNA cloning vector comprising the functionally dependent second plasmid of claim 1.

18. The recombinant DNA cloning vector of claim 17 which is selected from the group consisting of plasmids pEL7.1, pEL7.2, pEL7.3, pEL7.4, pEL7.5, pEL7.6, pEL7.7, and pEL7.8.

19. The recombinant DNA cloning vector of claim 18 which is plasmid pEL7.1.

20. The recombinant DNA cloning vector of claim 18 which is plasmid pEL7.2.

21. The recombinant DNA cloning vector of claim 18 which is plasmid pEL7.3.

22. The recombinant DNA cloning vector of claim 18 which is plasmid pEL7.4.

23. The recombinant DNA cloning vector of claim 18 which is plasmid pEL7.5.

24. The recombinant DNA cloning vector of claim 18 which is plasmid pEL7.5.

25. The recombinant DNA cloning vector of claim 18 which is plasmid pEL7.7.

26. The recombinant DNA cloning vector of claim 18 which is plasmid pEL7.8.

27. A novel recombinant DNA cloning vector comprising:
   (a) a functional *E. coli* replicon containing and antibiotic resistance conferring restriction fragment of an *E. coli* plasmid, and
   (b) a restriction fragment of a member of the pair of recombinant DNA cloning vectors recited in claim 1, subject to the limitation that said vector is functionally dependent upon plasmid pEL7 when transformed into *Streptomyces*.

28. The recombinant DNA cloning vector of claim 27 wherein the restriction fragment of the *E. coli* plasmid is the BamHI restriction fragment of plasmid pBR322.

29. The recombinant DNA cloning vector of claim 28 which is plasmid pLR5.

30. The recombinant DNA cloning vector of claim 28 which is plasmid pLR7.

31. The recombinant DNA cloning vector of claim 28 which is plasmid pLR9.

32. The recombinant DNA cloning vector of claim 28 which is plasmid pLR11.

33. A transformed restrictionless host cell selected from the group consisting of restrictionless cells of *Streptomyces, Streptosporangium, Actinoplanes, Nocardia, Micromonospora, Bacillus,* and *Staphylococcus* comprising a pair of recombinant DNA cloning vectors of claim 1.

34. The transformed restrictionless host cell of claim 33 in which the pair of recombinant DNA cloning vectors comprises plasmid pEL7 and a plasmid selected from the group consisting of plasmids pEL7.1, pEL7.2, pEL7.3, pEL7.4, pEL7.5, pEL7.6, pEL7.7, and pEL7.8.

35. A transformed restrictionless host cell selected from the group consisting of restrictionless cells of *Streptomyces, Streptosporangium, Actinoplanes, Nocardia, Micromonospora, Bacillus,* and *Staphylococcus* comprising a recombinant DNA cloning vector of claim 12.

36. A transformed host cell of claim 33 which is *Streptomyces*.

37. The transformed host cell of claim 34 which is *Streptosporangium*.

38. The transformed host cell of claim 34 which is *Actinoplanes*.

39. The transformed host cell of claim 34 which is *Nocardia*.

40. The transformed host cell of claim 34 which is *Micromonospora*.

41. The transformed host cell of claim 34 which is *Bacillus*.

42. The transformed host cell of claim 34 which is *Staphylococcus*.

43. The transformed host cell of claim 34 which is *Streptomyces*.

44. The *Streptomyces* of claim 43 which is *Streptomyces fradiae*.

45. The Streptomyces of claim 43 which is *Streptomyces aureofaciens*.

46. The *Streptomyces* of claim 43 which is *Streptomyces coelicolor*.

47. The transformed host cell of claim 34 which is Streptomyces ambofaciens/pEL7, pEL7.1.

48. The transformed host cell of claim 34 which is Streptomyces ambofaciens/pEL7, pEL7.2.

49. The transformed host cell of claim 34 which is Streptomyces ambofaciens/pEL7, pEL7.3.

50. The transformed host cell of claim 34 which is Streptomyces ambofaciens/pEL7, pEL7.4.

51. The transformed host cell of claim 34 which is Streptomyces ambofaciens/pEL7, pEL7.5.

52. The transformed host cell of claim 34 which is Streptomyces ambofaciens/pEL7, pEL7.6.

53. The transformed host cell of claim 34 which is Streptomyces ambofaciens/pEL7, pEL7.7.

54. The transformed host cell of claim 34 which is Streptomyces ambofaciens/pEL7, pEL7.8.

55. The transformed host cell of claim 35 which is Streptomyces ambofaciens/pEL7.

56. A transformed restrictionless host cell selected from the group consisting of *E. coli* and *Streptomyces* comprising the recombinant DNA cloning vector of claim 27 subject to the limitation that when said transformed host cell is *Streptomyces*, said vector is functionally dependent upon plasmid pEL7.

57. The transformed host cell of claim 56 wherein the restriction fragment of the *E. coli* plasmid is the BamHI restriction fragment of plasmid pBR322.

58. The transformed host cell of claim 57 which is *E. coli*.

59. The transformed host cell of claim 57 which is *E. coli* K12 HB101/pLR7.

60. The transformed host cell of claim 57 which is *E. coli* K12 HB101/pLR9.

61. The transformed host cell of claim 57 which is *E. coli* K12 HB101/pLR11.

62. The transformed host cell of claim 57 which is *E. coli* K12 HB101/pLR5.

63. The transformed host cell of claim 57 which is *E. coli* K12 HB101/pLR6.

64. The transformed host cell of claim 57 which is *Streptomyces*.

65. The transformed host cell of claim 64 which is selected from the group consisting of Streptomyces ambofaciens/pEL7, pLR5, and Streptomyces ambofaciens/pEL7, pLR7.

66. The transformed host cell of claim 64 which is Streptomyces ambofaciens/pEL7, pLR5.

67. The transformed host cell of claim 64 which is Streptomyces ambofaciens/pEL7, pLR7.

68. The transformed restrictionless host cell of claim 56 which is *E. coli* K12.

69. The transformed restrictionless host cell of claim 56 which is *E. coli* K12 HB 101.

70. The transformed restrictionless host cell of claim 56 which is *Streptomyces ambofaciens*.

* * * * *

UNITED STATES PATENT AND TRADEMARK OFFICE
CERTIFICATE OF CORRECTION

PATENT NO. : 4,416,994
DATED : November 22, 1983
INVENTOR(S) : Walter M. Nakatsukasa, Jeffrey T. Fayerman, James A. Mabe It is certified that error appears in the above—identified patent and that said Letters Patent is hereby corrected as shown below:

In column 4, line 23, delete the first listed "pBR324".

In column 4, line 65, "IS. tenebrarius" should be changed to -- S. tenebrarius --.

In column 5, line 30, "(alnkacidin, borrelidin)" should be changed to -- (lankacidin, borrelidin) --.

In column 9, line 4, "11 1. 11." should be changed to -- 1.11. --.

In column 18, line 68, "pEL7.5" should be changed to -- pEL7.6 --.

Signed and Sealed this

Twenty-third Day of April 1985

[SEAL]

Attest:

DONALD J. QUIGG

Attesting Officer     Acting Commissioner of Patents and Trademarks